(12) United States Patent
Robinson et al.

(10) Patent No.: US 7,008,393 B2
(45) Date of Patent: Mar. 7, 2006

(54) BLOOD PROCESSING SYSTEM

(75) Inventors: Thomas C. Robinson, Oakland, CA (US); Thomas P. Sahines, Milpitas, CA (US); Richard R. D'Elia, San Mateo, CA (US); Robert K. Fernandez, Campbell, CA (US); Frank Hickman, Sunnyvale, CA (US)

(73) Assignee: Mission Medical, Inc., Fremont, CA (US)

( * ) Notice: Subject to any disclaimer, the term of this patent is extended or adjusted under 35 U.S.C. 154(b) by 235 days.

(21) Appl. No.: 10/265,297

(22) Filed: Oct. 3, 2002

(65) Prior Publication Data

US 2003/0138349 A1 Jul. 24, 2003

Related U.S. Application Data

(62) Division of application No. 09/419,216, filed on Oct. 15, 1999, now Pat. No. 6,695,803.

(60) Provisional application No. 60/104,557, filed on Oct. 16, 1998.

(51) Int. Cl.
  *A61M 37/00* (2006.01)
  *A61M 31/00* (2006.01)
  *C02F 1/44* (2006.01)

(52) U.S. Cl. ............... 604/6.01; 604/65; 604/6.09; 210/600; 210/645; 210/739

(58) Field of Classification Search ............ 210/252, 210/645–47, 739, 741, 744–746, 97, 203, 210/433.1, 500.21; 604/4.01, 5.01, 6.01, 604/6.09, 6.04–6.06, 6.11, 6.15, 6.16, 65–67; 422/44
See application file for complete search history.

(56) References Cited

U.S. PATENT DOCUMENTS

| 4,191,182 A | * | 3/1980 | Popovich et al. .......... 604/6.01 |
| 4,369,117 A | | 1/1983 | White |
| 4,379,452 A | | 4/1983 | DeVries |
| 4,436,620 A | | 3/1984 | Bellotti et al. |

(Continued)

FOREIGN PATENT DOCUMENTS

WO 98/22165 5/1998

OTHER PUBLICATIONS

Supplementary Partial Search Report from European Patent Office, dated May 12, 2005.

*Primary Examiner*—Patricia Bianco
*Assistant Examiner*—Leslie R Deak
(74) *Attorney, Agent, or Firm*—Pillsbury Winthrop Shaw Pittman LLP

(57) ABSTRACT

A blood processing system (2), includes a housing (4), to which a user control panel is mounted, having an access opening (47) therein. A cassette assembly (22), mounted to the housing for movement between a use position covering the access opening and a cassette-replacement position, includes a cassette holder and cassette (26) removably mounted to the holder. The cassette includes in part by tubing aligned with a through-hole (45) in the cassette. A door (34) is mounted to the housing for movement between a latched position, capturing the cassette between the panel and the door, and a released position. Independently-driven roller assemblies (46, 54, 72) pass part-way through the access opening to capture first tubing portions (44A, 52A, 68A) between the roller tracks (100, 102, 104) and the roller assemblies for peristaltic pumping of fluid. A number of movable pinch elements (48, 80, 90, 96) are extendable through the front panel to selectively pinch the tubing against the door and thus seal the tubing.

19 Claims, 21 Drawing Sheets

U.S. PATENT DOCUMENTS

| | | |
|---|---|---|
| RE31,688 E | 9/1984 | Popovich et al. |
| RE32,089 E | 3/1986 | Blatt et al. |
| 4,617,009 A | 10/1986 | Ohlin et al. |
| 4,637,813 A | 1/1987 | DeVries |
| 4,648,866 A | 3/1987 | Malbrancq et al. |
| 4,655,742 A | 4/1987 | Vantard |
| 4,680,025 A | 7/1987 | Kruger et al. |
| 4,687,580 A | 8/1987 | Malbrancq et al. |
| 4,747,952 A | 5/1988 | Nakano et al. |
| 4,800,022 A | 1/1989 | Leonard |
| 4,806,247 A | 2/1989 | Schoendorfer et al. |
| 4,828,543 A | 5/1989 | Weiss et al. |
| 4,855,057 A | 8/1989 | Ohnishi et al. |
| 4,855,063 A | 8/1989 | Carmen et al. |
| 4,863,590 A | 9/1989 | Ohnishi et al. |
| 4,871,462 A | 10/1989 | Fischel et al. |
| 4,886,487 A | 12/1989 | Solem et al. |
| 4,897,185 A | 1/1990 | Schuyler et al. |
| 4,898,573 A | 2/1990 | Takenaka et al. |
| 4,911,703 A | 3/1990 | Lysaght et al. |
| 4,915,848 A | 4/1990 | Carmen et al. |
| 4,935,002 A | 6/1990 | Gordon |
| 4,964,847 A | 10/1990 | Prince |
| 4,964,976 A | 10/1990 | Lysaght et al. |
| 4,980,054 A | 12/1990 | Lavender |
| 4,981,596 A | 1/1991 | Shiino et al. |
| 4,985,153 A | 1/1991 | Kuroda et al. |
| 5,055,198 A | 10/1991 | Shettigar |
| 5,069,792 A | 12/1991 | Prince et al. |
| 5,104,526 A | 4/1992 | Brown et al. |
| 5,112,298 A | 5/1992 | Prince et al. |
| 5,114,580 A | 5/1992 | Ahmad et al. |
| 5,141,490 A | 8/1992 | Fujii et al. |
| 5,171,456 A | 12/1992 | Hwang et al. |
| 5,188,588 A | 2/1993 | Schoendorfer et al. |
| 5,232,437 A | 8/1993 | Lysaght et al. |
| 5,242,384 A | 9/1993 | Robinson et al. |
| 5,298,171 A | 3/1994 | Biesel |
| 5,364,533 A | 11/1994 | Ogura et al. |
| 5,372,709 A | 12/1994 | Hood |
| 5,394,732 A | 3/1995 | Johnson et al. |
| 5,437,598 A | 8/1995 | Antwiler |
| 5,445,506 A | 8/1995 | Afflerbaugh et al. |
| 5,456,835 A | 10/1995 | Castino et al. |
| 5,462,416 A | 10/1995 | Dennehey et al. |
| 5,549,834 A | 8/1996 | Brown |
| 5,580,465 A | 12/1996 | Pall et al. |
| 5,581,687 A | 12/1996 | Lyle et al. |
| 5,637,082 A | 6/1997 | Pages et al. |
| 5,665,238 A | 9/1997 | Whitson et al. |
| 5,746,708 A | 5/1998 | Giesler et al. |
| 5,769,811 A | 6/1998 | Stacey et al. |
| 5,795,317 A | 8/1998 | Brierton et al. |
| 5,817,042 A | 10/1998 | Langley et al. |
| 5,837,150 A | 11/1998 | Langley et al. |
| 5,858,238 A | 1/1999 | McRea et al. |
| 5,865,785 A | 2/1999 | Bischof |
| 5,866,007 A | 2/1999 | Whitson et al. |
| 5,870,805 A | 2/1999 | Kandler et al. |
| 5,879,624 A | 3/1999 | Boehringer et al. |
| 5,910,252 A * | 6/1999 | Truitt et al. ............. 210/645 |
| 5,921,950 A | 7/1999 | Toavs et al. |
| 5,941,842 A | 8/1999 | Steele et al. |
| 5,989,423 A | 11/1999 | Kamen et al. |
| 6,068,970 A | 5/2000 | Hosono et al. |
| 6,080,322 A | 6/2000 | Deniega et al. |
| 6,113,554 A | 9/2000 | Gilcher et al. |
| 6,113,782 A | 9/2000 | Leonard |
| 6,129,656 A | 10/2000 | Blakeslee et al. |
| 6,186,752 B1 | 2/2001 | Deniega et al. |
| 6,217,540 B1 | 4/2001 | Yazawa et al. |
| 6,245,244 B1 | 6/2001 | De Rooij |
| 6,251,284 B1 | 6/2001 | Bischof et al. |
| 6,258,321 B1 | 7/2001 | Van Driel et al. |
| 6,270,673 B1 | 8/2001 | Belt et al. |
| 6,315,707 B1 | 11/2001 | Smith et al. |
| 6,325,775 B1 | 12/2001 | Thom et al. |
| 6,348,156 B1 | 2/2002 | Vishnoi et al. |
| 6,398,955 B1 | 6/2002 | Fumiyama et al. |
| 6,495,039 B1 | 12/2002 | Lee et al. |
| 6,527,957 B1 | 3/2003 | Deniega et al. |
| 6,730,055 B1 * | 5/2004 | Bainbridge et al. ......... 604/6.04 |
| 2002/0028155 A1 | 3/2002 | Dolecek et al. |
| 2002/0062100 A1 | 5/2002 | Pierce et al. |
| 2002/0123154 A1 | 9/2002 | Burshteyn et al. |
| 2003/0106861 A1 | 6/2003 | Gibbs et al. |

* cited by examiner

BLOOD PROCESSING SYSTEM

CROSS-REFERENCE TO RELATED APPLICATION

This application is a divisional application of U.S. application Ser. No. 09/419,216 filed Oct. 15, 1999, which is incorporated by reference herein.

BACKGROUND OF THE INVENTION

Blood processing systems are used for a range of purposes. They are used, for example, to collect blood from donors, for autotransfusion where blood lost by a patient during an operation is collected, cleaned and reintroduced into the patient's circulatory system, to prepare collected blood for freezing, to deglycerolize frozen thawed red cells, for washing red blood cells and for washing frozen thawed platelets.

There are features which would be very desirable with virtually all blood processing systems but are not provided by current systems. To understand these desirable features one must first fully appreciate the practical aspects of the blood processing technology as discussed below. The desirable features are small size of equipment, acceptably priced disposables, automatic operation, protection from operator error, protection from equipment error, speed of operation and complete one-step processing.

Considering first a blood collection system, the collection of blood from donors takes place both at blood banks and via use of mobile units during so-called blood drives with the mobile unit collection often exceeding that at the blood banks. Accordingly, it is desirable to have relatively compact systems so that a larger number can be easily transported to the site of blood collection. Fast blood collection is desirable since if donor comfort is increased by reducing the donation time it is easier to attract donors.

Whole blood has usually been collected from a donor via gravity flow; alternatively, use of a blood removal roller pump has been used to aid collection from a donor. The whole blood was then transported to a blood processing facility and centrifuged to separate the plasma from the erythrocytes. In some instances a leukocyte filter was used on the whole blood or on red cells to reduce the chance for undesirable patient reactions to donor leukocytes when donor red cells were later transfused into a patient. This whole blood collection procedure suffers from a number of drawbacks. One major drawback is that the procedure is highly dependent on the skill of the operator taking the blood donation, thus requiring extensive and expensive training of operators. Also, the current procedures require nearly constant operator attention, thereby limiting the amount of blood which can be safely collected in a given time period; i.e., the operator can only safely oversee a limited number of blood donations at any one time. There is also a drawback that having several people handle the whole blood as it is collected and separated into its component parts increases the chance of operator error. Another drawback is that the several steps required, even if carried out by a single operator, increase the risk of contamination of the whole blood and of its separated component parts.

An apparatus has also been proposed which has the capability of fully processing blood at the collection site but it is relatively bulky and requires the use of a built in rotating centrifuge. The apparatus has a number of limitations which include cost, relative bulkiness, the possibility of leaks at rotating seals, relatively slow speed since all blood must be collected prior to the beginning of separation into components, etc., and the requirement of close operator supervision. The apparatus is disclosed in U.S. Pat. Nos. 5,651,766; 5,728,060; and 5,733,253.

Another blood processing system, called an intraoperative autotransfusion system, is commonly used during certain operations, such as orthopedic surgery and open-heart surgery, when a great deal of blood can be lost by the patient. In autotransfusion the lost (shed) blood along with air, particulate matter and diluting solvents are collected. The air, solvents, and particulate matter are removed. The cells are washed and the hematocrit is increased to a desired level such as that normally present in the body (about 40%). The resulting blood-cell suspension is transfused back into the patient. Autotransfusion reduces the cost and problems (incompatibility and infection) associated with blood bank blood. It would be desirable to have a relatively small size unit since operating rooms constitute a highly crowded environment. Furthermore, automatic operation is desirable as it allows medical personnel to attend to other matters while the autotransfusion unit carries out the desired task of collecting and cleansing red blood cells for re-infusion. Low cost of disposables is necessary since if the cost is too high even the technically best available system may not be used. The system set forth in U.S. Pat. Nos. 5,242,384 and 5,423,738 is adapted for automated autotransfusion but the high cost of the complex disposable and its tangential flow separator has prevented this system from wide commercial acceptance.

Another type of blood processing system is the thawed blood processing system. It is intended to remove glycerol and free plasma hemoglobin from thawed frozen red blood cells. It is primarily used by the military on land and aboard ship to provide red cells in emergency situations. The military has stockpiled a large number of units of blood, all of one universal donor type, for this purpose. Frozen blood is also commonly used when a patient undergoing elective surgery desires to stockpile his or her own blood for use during the surgery. Frozen blood is also used to supply rare blood types.

One of the problems with using frozen blood is that it requires that some type of agent be added to the red blood cells to allow them to be safely frozen; glycerol has commonly been used for this purpose. Also, some red blood cells are damaged by the freezing process. Once thawed, these damaged red blood cells release free plasma hemoglobin. Both the glycerol and free plasma hemoglobin must be reduced to safe levels in the thawed blood and saline and a red cell storage solution must be added to the thawed blood before transfusion into a patient. Once again, small size, automatic operation and low cost are important factors.

Another blood processing system is used for washing red blood cells. Blood is collected, separated into its components and concentrated red blood cells are stored in a bag which contains the storage solution to preserve the red cells. Once again, small size, automatic operation and low cost are important factors.

A further blood processing system is used to wash frozen thawed platelets. In this system the platelets are frozen with, for example, DMSO, and possibly other preservatives. When the frozen platelets are thawed, the DMSO and possibly other preservatives are preferably washed from the platelets before the platelets can be used.

U.S. Pat. Nos. 5,670,312; 5,460,493; 5,311,908; 5,273,517; 5,195,960; 4,985,153; and 4,385,630 disclose various types of blood processing systems and system components.

SUMMARY OF THE INVENTION

One aspect of the present invention is directed to a blood processing system designed for the automatic or semi-automatic processing of blood during processing procedures such as blood collection from a donor, intraoperative autotransfusion, thawed red blood cells processing, washing fresh red blood cells, and washing thawed platelets. The system provides for the use of an easily removable and replaceable cassette which contains all of the disposable components.

The blood processing system includes a housing having a panel; user controls are preferably mounted to the panel. The system also includes a cassette assembly mounted to the housing adjacent to an access opening in the panel for movement between a use position, adjacent to and covering the access opening, and a cassette-replacement position. The cassette assembly includes a cassette holder and cassette removably mounted to the holder. The cassette includes a cassette body having one or more through-holes. The cassette also includes flow channels defined at least in part by tubing, the tubing having first and second portions aligned with the through-holes. The cassette preferably carries all of the disposable elements, such as filter, separator, and tubing.

The system also includes a fastening assembly, typically a door, movably mounted to the housing for movement between a latched position, capturing the cassette between the panel and the door, and a released position. In an embodiment of the invention the door has roller tracks positioned to engage the first tubing portion when the cassette assembly is in the use position and when the door is in the latched position. A roller pump drive assembly is mounted within the housing and includes independently-driven roller assemblies. Each roller assembly includes a number of circumferentially positioned rollers. Each roller assembly is preferably mounted for rotation about a common axis. Each roller assembly is located to be aligned with the access opening and aligned with a corresponding first tubing portion. The first tubing portions in this embodiment are captured between the roller tracks on the door and the roller assemblies so that fluid is pumped through the first tubing portions by rotation of the roller assemblies.

A number of movable pinch elements are mounted within the housing and are aligned with the second tubing portions. The pinch elements are movable to selectively pinch the second tubing portions against the door, thus closing the tubing, when the door is in the latched position. A controller is operably coupled to the operator controls, roller pump drive assembly, cassette assembly and pinch elements.

A blood processing system made according to an embodiment of the invention is preferably designed so that the pumping rate and pumped volume are controlled by monitoring the pressure or other parameters within the system. When the system is used to pump blood from a donor, it is desired to pump the blood from the donor as fast as possible without harming the donor, such as collapsing a blood vessel, or damaging the blood being withdrawn. With the present invention the pumping rate of blood pumped from a donor can be determined and controlled by, for example, monitoring the drop in pressure along a portion of the flow path within the system and adjusting the pump speed to achieve a desired pressure level. By doing so, the pumping pressure can be maintained in an optimal range for a donor so that the vessel is not collapsed.

The system can be designed to automatically collect blood and shut down after collecting a chosen volume.

The hollow fiber separator is used to separate fluid from a cellular suspension (blood or blood components) flowing through it. A preferred hollow fiber separator includes a number of microporous hydrophilic hollow fibers arranged in a bundle of parallel fibers. The porous walls of these fibers have pore size that on average is about 0.2 to 0.5 microns in diameter. The fiber bundle is placed in a housing that closely surrounds the outside of this bundle. The ends of this bundle are potted and sealed with a liquid material such as polyurethane that solidifies and fills the spaces between the housing and all of the fibers. Each end of the bundle is then cut through the potting material at the ends of the housing. This exposes the lumens of the fibers. End caps are secured and sealed to each end of the housing. A port in each end cap leads fluid into or out of the chamber formed by the inside of the end cap and the cut ends of the fibers. Fluid containing cells (red cells or platelets) flows in one end cap, through the lumens of the fibers, and out the other end cap. A port in the wall of the housing is used to remove fluid which passes through the pores of the fibers from the outside surfaces of the fibers. This removed fluid typically comes from the fluid flowing through the lumens of the fibers. The removed fluid consists of a liquid containing salts, free plasma hemoglobin, possibly anticoagulant, possibly glycerol, other dissolved matter, and small particulates. The removal process is called tangential or cross-flow separation. The high velocity of flow inside the fibers keeps cells and other material away from the wall and prevents pore plugging or layering that can decrease removed fluid flow rates. The pressure levels at the end cap entrance and exit of the separator and at the removed fluid port affect removed fluid flow rate. A pump can be used to control this flow rate. Increases in the pressure differential across the fiber wall can increase removed fluid flow rate up to the point that significant and undesirable cellular layering occurs on the inside surfaces of the fibers which reduces removed fluid flow rate. The pressure differential and blood flow rate are controlled to prevent this.

When whole blood is concentrated by a hollow fiber separator and separated into red cells and plasma, plasma is the removed fluid. A recirculation process is preferably used to concentrate the red cells to a high hematocrit and to separate the plasma into a bag.

The washing of red cells or platelets preferably occurs by separating the removed fluid or waste from the cells with waste fluid flowing through the walls of the hollow fibers, out the plasma port, and into a waste bag. Saline or another solution is added at the cellular flow exit of the separator at a flow rate essentially equal to the waste flow. The saline is made to mix well with the cellular flow in a mixing tee and tubing. Then the cellular flow enters into the recirculation bag, goes inside the recirculation bag, goes out of the recirculation bag, and enters into the separator at a constant hematocrit, perhaps 45%. The recirculation bag can be mixed by mechanical manipulation to ensure a constant hematocrit is maintained in the bag and that the concentration of removed matter (e.g. free plasma hemoglobin; anticoagulant; glycerol) is uniform within the recirculation bag to ensure consistent performance. The wash process is then a continuous waste removal and saline or wash fluid replacement process that rapidly decreases the concentration of removed matter in the recirculation bag. Higher recirculation bag hematocrits, higher cellular fluid flow rates, and higher changes in hematocrit across the separator tend to improve the efficiency and speed of removal.

The most expensive component of the cassette is typically the plasma separator, such as a hollow fiber separator. One of the primary aspects of the invention is the recognition that a less expensive separator can be used if the system is designed so that blood can be selectively recirculated to pass all or part of the blood through the separator more than once until the desired separation, typically measured by hematocrit, has been achieved. Doing so reduces the cost of the disposable cassette without reducing the effectiveness of the system. Recirculation can be achieved, for example, using appropriate pinch valves and the main blood pump or with the aid of a separate blood recirculation pump. Recirculation may, or may not, involve the use of a recirculated blood reservoir.

A primary advantage of the invention is the interchangeability of the components and the ease of modifying the invention to accommodate different blood processing systems. For example, it is often possible to modify the blood processing system to accomplish different tasks, for example blood collection, autotransfusion, thawed blood processing, or red cell washing, by simply modifying the specific computer program used to run the controller, and changing the number and types of bags, where the bags are hung and how the bags are hooked up to the remainder of the system. Only the disposable cassette will usually be specially constructed for a particular procedure or process. Because the same general system can be used for a wide variety of specific blood processing tasks, economies of scale, and thus lower user cost, can be achieved.

Another advantage of, and a further aspect of, the invention is that the cassette can be easily tested to ensure that it is leak-free, which is a very necessary attribute for the system. This can be accomplished simply by pressurizing the flow channels and determining the rate of any drop-off in pressure. Any unacceptable cassettes can be either discarded or reworked prior to being shipped to solve the problem.

It is important that the system not be run when, for example, the source of blood or of a supplemental fluid, such as saline or anticoagulant, is not connected to flow channels of the cassette, or when the source is empty, or when a valve is incorrectly closed, or when a line is crimped. Various detectors non-invasively provide the necessary signals to the controller so that the controller can shut down pumping by halting the rotation of the roller assemblies and/or closing pinch valves should any of these problems occur. Doing so helps reduce the negative results of operator error or product failure.

It is important that the cassette be positioned so that tubing is not improperly engaged in the latched position. It is important to provide structure to accomplish this and, at the same time, properly align the tubing on the cassette relative to the roller assemblies and the pinch elements for proper operation. This is aided by ensuring that the cassette is properly positioned in the cassette holder so that with the cassette assembly in the use position and the door in the latched position, all elements are properly aligned. The proper positioning of the cassette in the cassette holder is aided by the fact that gravity helps keep the cassette properly and fully engaged within and supported by the cassette holder. Also, or as an alternative, appropriate guide elements, such as tapered pins, extending from the housing or the cassette can be used to engage appropriately located guide holes in the cassette or the housing when the cassette assembly is in the use position.

Accurate but non-invasive pressure measurements taken along the flow channels are important to, for example, ensure correct and safe pressure levels and to control fluid flow rates by monitoring pressure drops across a pressure drop device such as a laminar flow tube. This can be achieved using sealed diaphragm pressure access ports along the flow channel; the pressures at such ports are preferably coupled to a pressure sensor which provides a pressure signal to the controller for each pressure access port monitored. Fluidly coupling the pressure sensor and the pressure access ports is preferably automatically made as the cassette is secured into its use position and the door is placed into its latched position.

It is also important to add anticoagulant to the blood and mix the two well. When blood is recirculated and stored in a recirculation reservoir, it is important in some uses to ensure that the blood is thoroughly mixed with inlet blood entering the reservoir along with a saline or other solution for effective red cell washing. This can be accomplished by automatically and mechanically manipulating the bag-type reservoir by, for example, flexing, kneading or punching the bag-type reservoir. Such mechanical manipulation of a bag-type reservoir simply and thoroughly mixes the contents of the bag but without any physical contact with the blood. Thorough mixing can, for example, also be accomplished by pumping from one reservoir into another reservoir or through the use of mechanical stirrers.

Mechanical bag manipulators preferably act on vertically-hung bags so that the contents of the bags can be mixed while processing without the need for special supports or alignments of the bags. While vertically-hung bags can have their contents mixed by shaking the entire bag support, this is not usually preferred because of problems caused by the shaking, such as loosening of fittings, noise, etc.

Other features and advantages will appear from the following description in which the preferred embodiments have been set forth in detail in conjunction with the accompanying drawings.

DESCRIPTION OF THE SPECIFIC EMBODIMENTS

Figure 1:
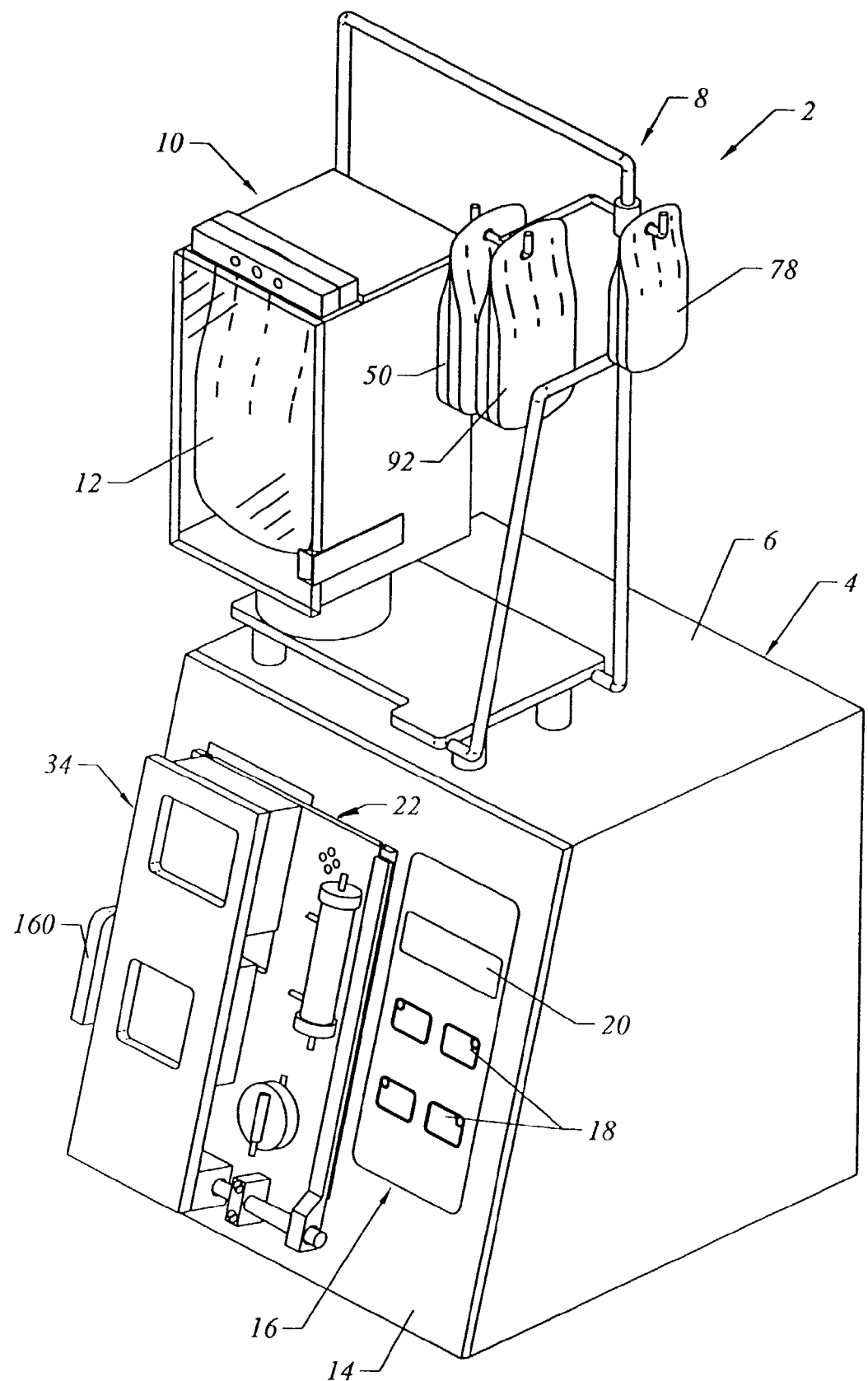
FIG. 1 is a simplified overall view of an automatic blood collection system made according to an embodiment of the invention showing a cassette assembly in the use position and the door in the latched position.

FIG. 1 illustrates an automatic blood collection system 2 made according to an embodiment of the invention. System 2 is a substantially fully automated system which swiftly, and with minimal operator handling and attention, automatically removes blood from a donor and separates the whole blood as taken into its component parts. System 2 includes a housing 4 having a top 6 supporting a bag hanger assembly 8. Bag hanger assembly 8 includes a mechanical bag manipulator 10 which is designed so that it can mechanically manipulate a storage bag 12, housed within manipulator 10 so as to help mix the contents of bag 12.

System 2 also includes a front panel 14 to which a user control panel 16 is mounted. User control panel 16 typically includes a number of input pads or buttons 18 and a display 20. While control panel 16 is preferably mounted to housing 4, it can alternatively be physically separated from the housing and operably coupled to the housing by, for example, cables.

Figure 2:
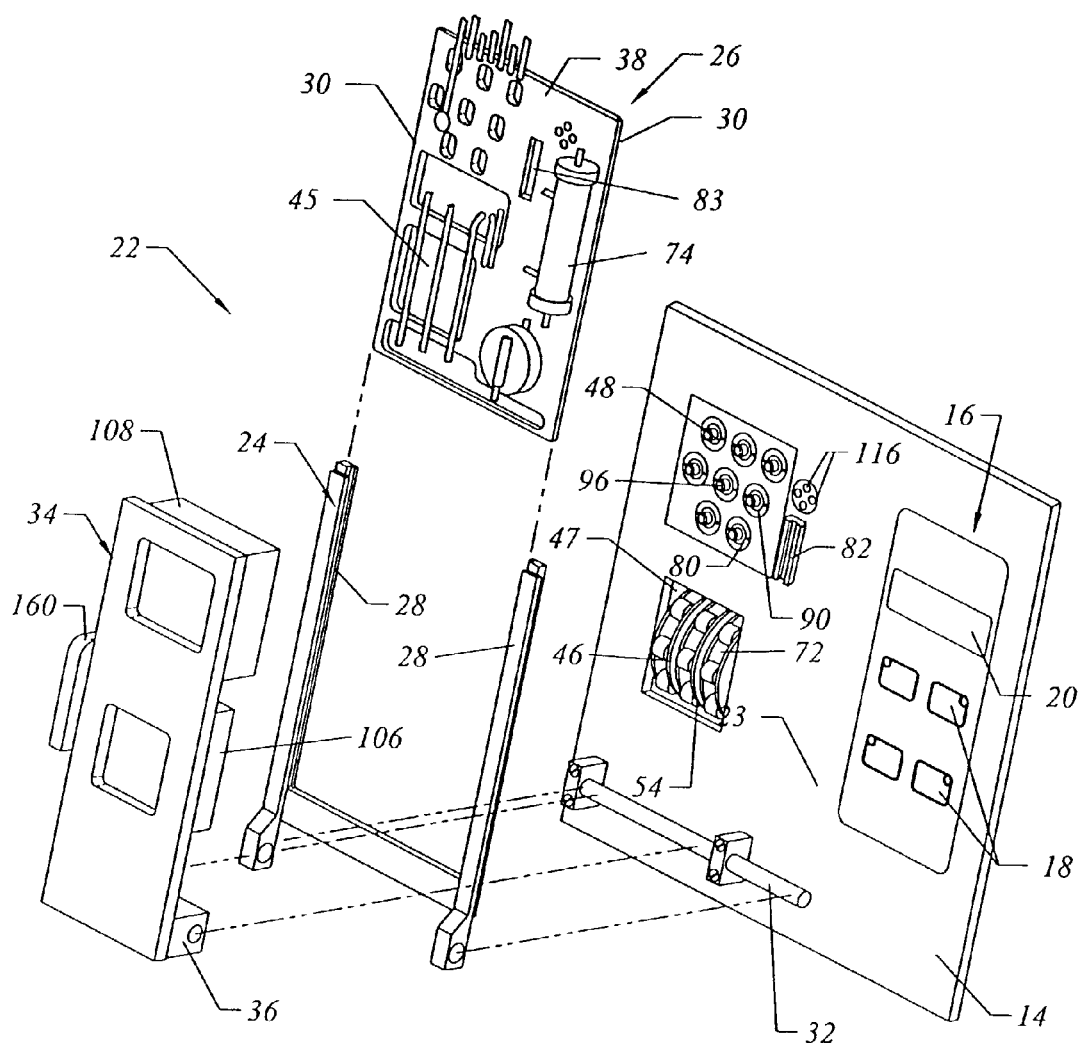
FIG. 2 is a simplified exploded isometric view of the panel, cassette assembly and door of the system of FIG. 1.

Referring now also to FIG. 2, system 2 is seen to include a cassette assembly 22, including a generally U-shaped cassette holder 24 and a removable, and typically disposable, cassette 26. Cassette holder 24 includes a pair of side rails 28 defining inwardly facing grooves within which the lateral edges 30 of cassette 26 slide. Cassette holder 24 is pivotally mounted to a support rod 32 mounted to and parallel with front panel 14. The orientation and configuration of cassette holder 24 and cassette 26 causes cassette 26 to be maintained fully housed within cassette holder 24 by gravity and by the friction between the lateral edges 30 of cassette and side rails 28 of holder 24.

System 2 further includes a door 34 having a mounting block 36 at the lower end. Door 34 is also pivotally mounted to front panel 14 through the use of support rod 32 passing through mounting block 36. Therefore, cassette assembly 22 and door 34 both pivot about a common axis defined by support rod 32.

Figure 3:
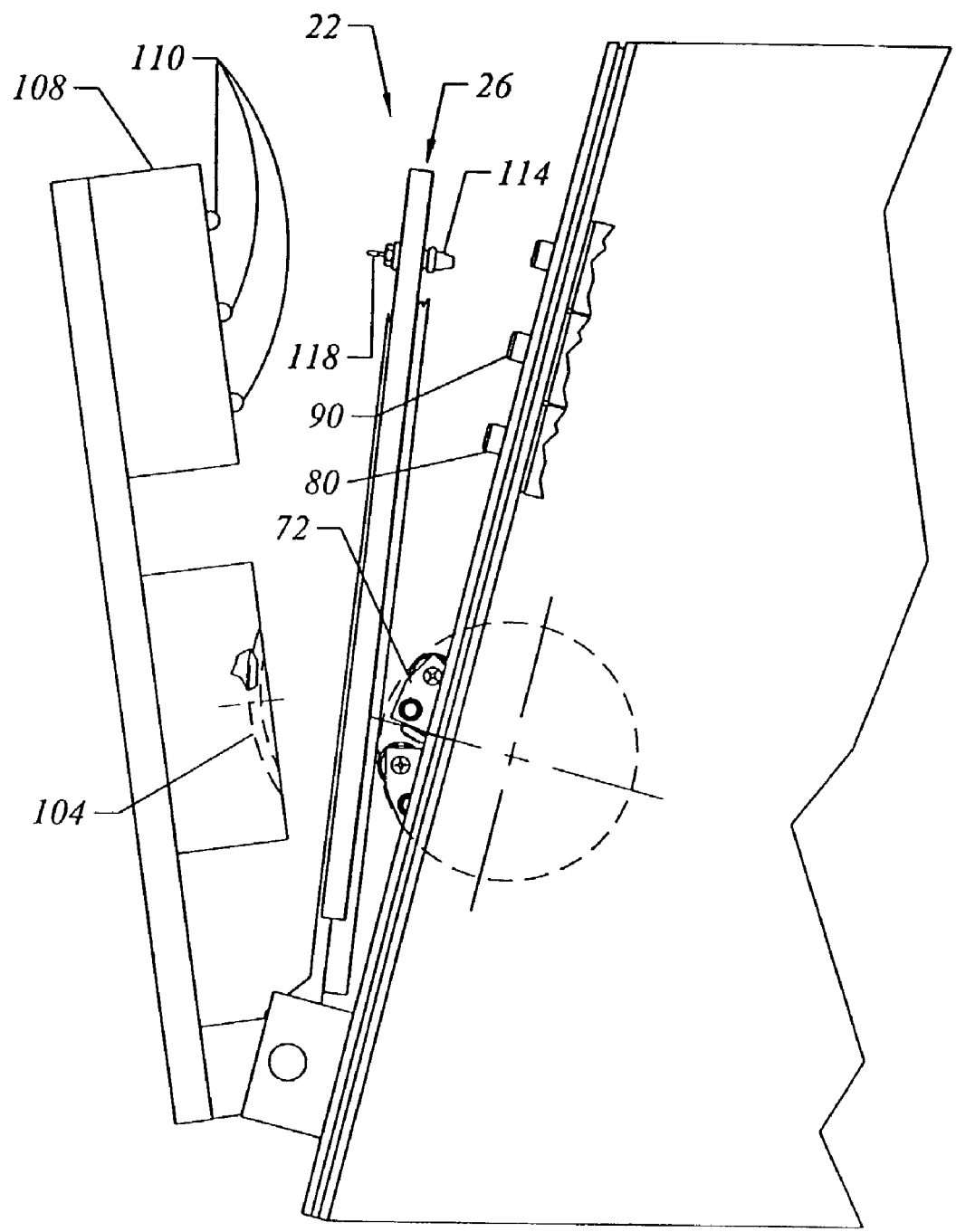
FIG. 3 is a side elevational view of the front panel portion of the system of FIG. 1 showing the door in a released position and the cassette assembly in a cassette replacement position.

Cassette assembly 22 can be pivoted between a use position, adjacent to front panel 4, as shown in FIG. 1, and a cassette replacement position, at which cassette assembly 22 is pivoted away from front panel 14, as illustrated in FIG. 3. Door 34 can be pivoted between a latched position, shown in FIG. 1, at which door 34 is latched to housing 4 thus capturing cassette 26 between door 34 and panel 14, and a released position, shown in FIG. 3, at which the door is pivoted away from panel 14 thus permitting the free access to cassette 26. Door 34 covers a portion of cassette 26 when in the latched position of FIG. 1.

Cassette 26 is designed for blood collection from a donor. Cassette 26 includes a body 38 which can be used for additional blood processing procedures as will be discussed in more detail below with reference to FIGS. 12 and 13.

Figure 2A:
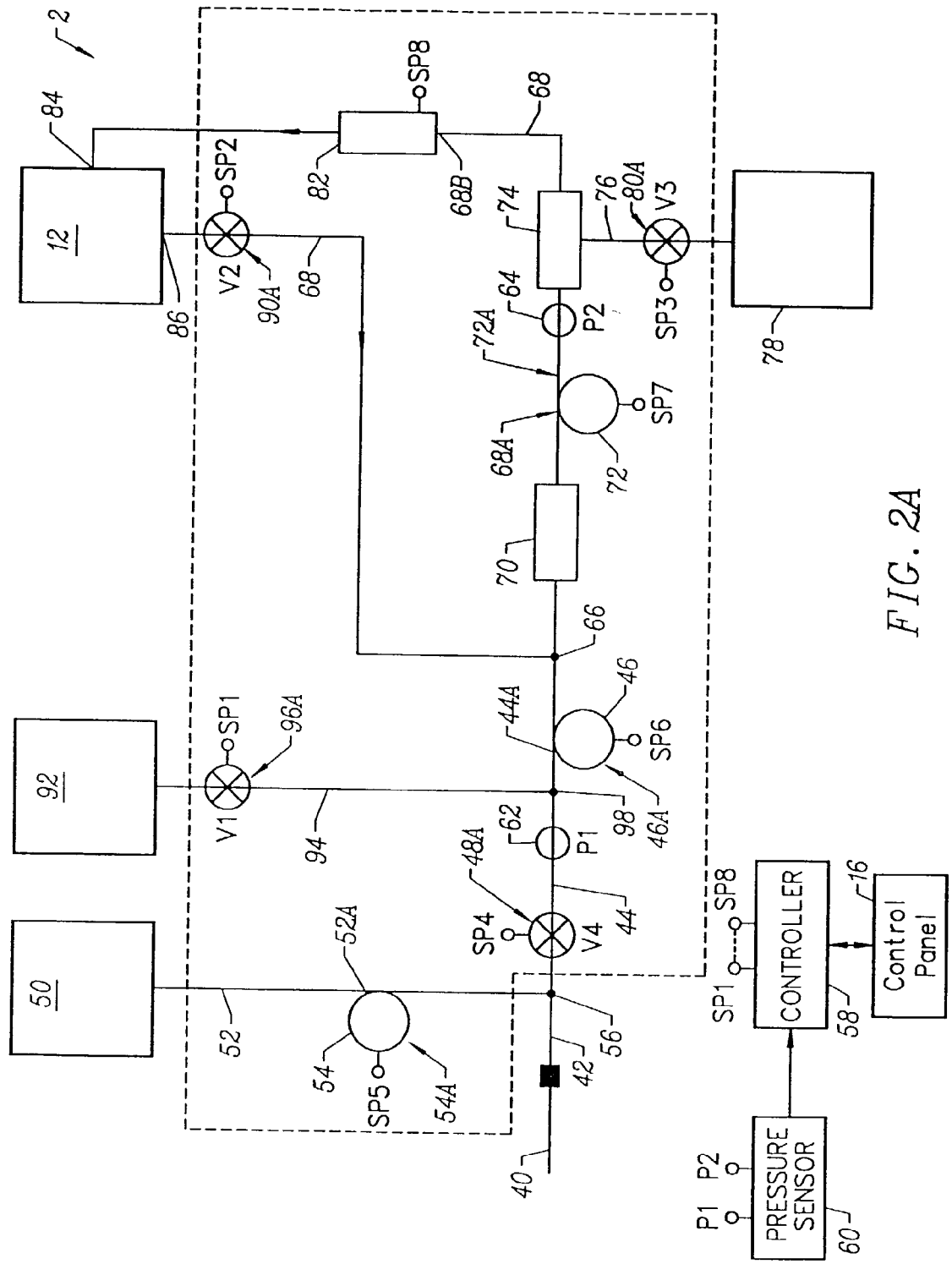
FIG. 2A is a schematic illustration of the automatic whole blood collection system of FIG. 1.

Blood processing system 2 will now be discussed with reference to a schematic representation of the system shown in FIG. 2A. System 2 uses three pumps 46A, 54A and 72A; each pump is made of a respective roller assembly 46, 54 and 72 which engages a respective tubing segment 44A, 52A, 68A (see also FIG. 5), the tubing segment being captured between the roller assembly and an associated roller track 100, 102, 104 (see FIGS. 3 and 4) on door 34 when the door is in the latched position of FIG. 1. With system 2, blood is pumped from the donor through a needle 40, inserted into an appropriate donor blood vessel, and through a line 42. Line 42 continues to cassette 26, the intersection of line 42 and the cassette indicated by a dashed line in FIG. 2A. Note that the lines or tubes coupling cassette 26 with needle 40 and the various bags shown in FIG. 1 are shown in FIG. 2A only for the sake of clarity of illustration in the other figures.

Figure 7:
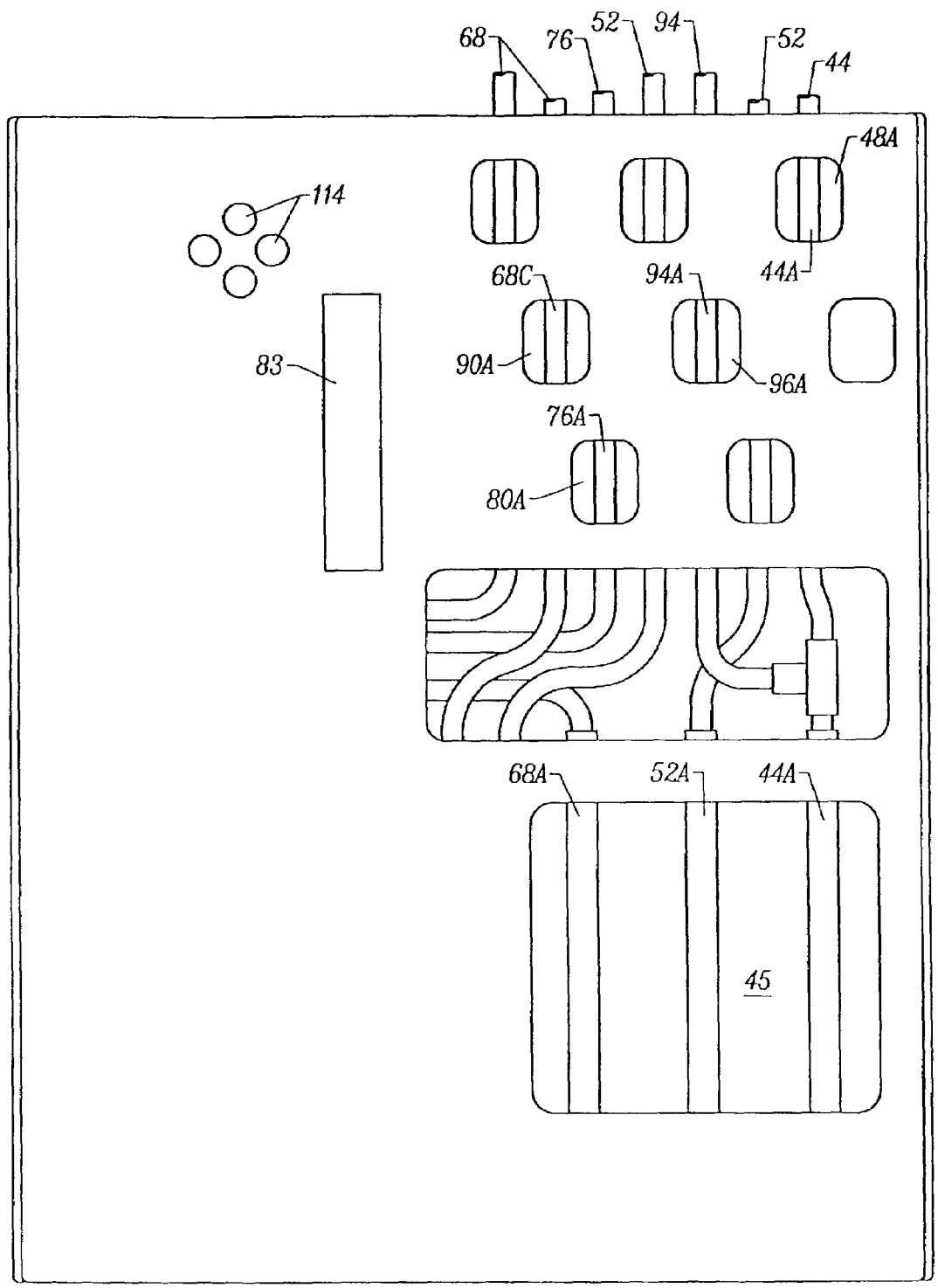
FIG. 7 is a view of the inner surface of the cassette of FIG. 3.
Figure 8:
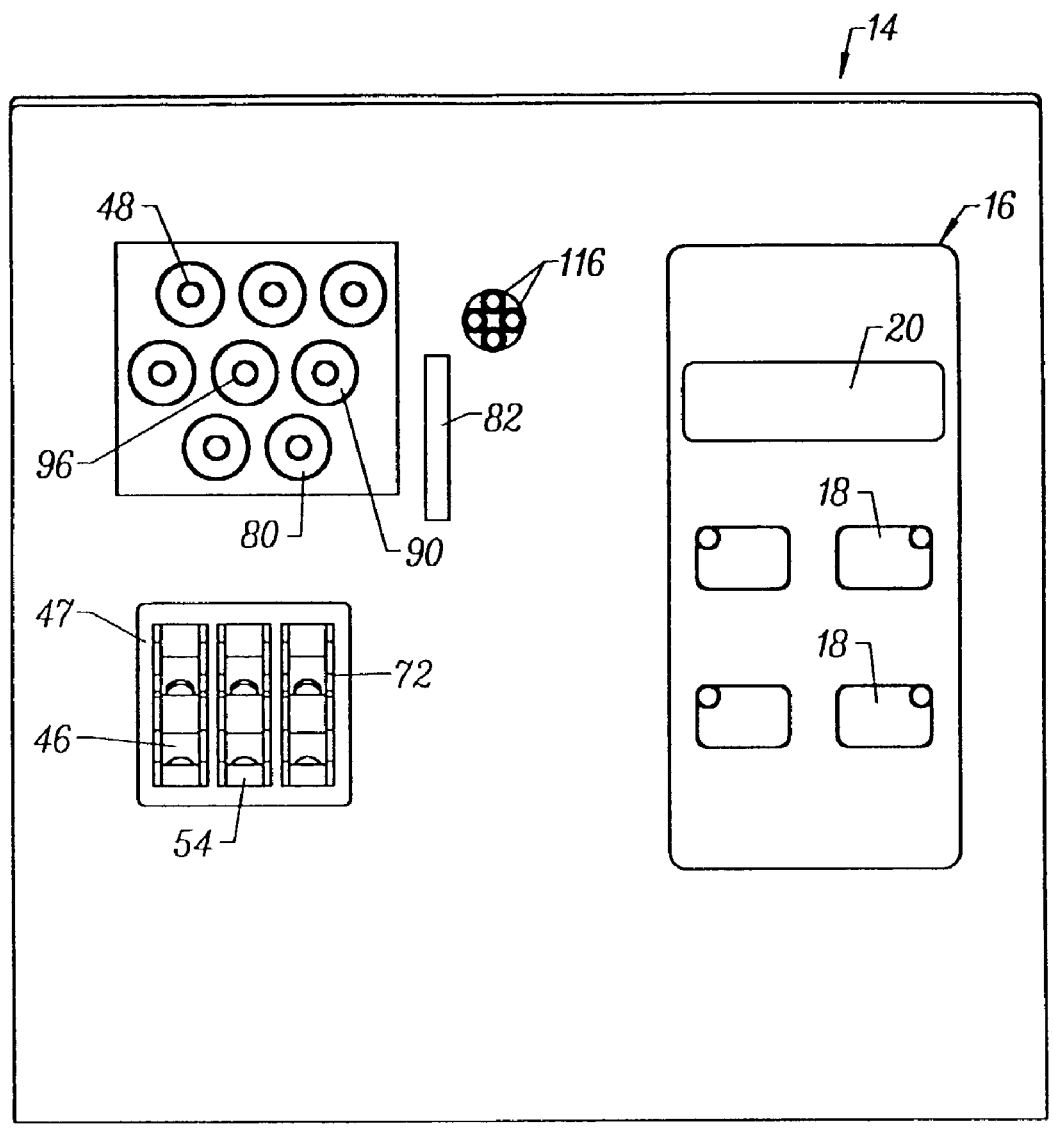
FIG. 8 is a plan view of the panel of FIG. 3 with the door and cassette assembly removed.

Line 42 continues within cassette 26 as line 44. A segment 44A of line 44, aligned with a through-hole 45 in cassette 26, is engaged by a blood pump roller assembly 46, which passes through an access opening 47 in panel 14, after line 44 passes a pinch valve plunger 48 (see FIGS. 2 and 8) at a plunger opening 48A (see FIGS. 5 and 7) in cassette body 38. System 2 includes four pinch valves 48A, 80A, 90A and 96A; each pinch valve is made up of a respective pinch valve plunger 48, 80, 90 and 96 which engages a tubing segment 44A, 76A, 68C and 94A (see FIGS. 5 and 7), the tubing segments being selectively pinched closed between the pinch valve plungers and an associated raised element 110 (see FIGS. 3 and 4) on door 34 when the door is in the latched position of FIG. 1.

Anticoagulant from an anticoagulant bag 50 passes along a line 52 within cassette 26. Anticoagulant is pumped at a metered rate corresponding to the rate of blood from the donor by an anticoagulant pump roller assembly 54 which engages a line segment 52A and delivers the anticoagulant to line 42 at a T coupling 56 external of cassette 26. Since the blood being processed is anticoagulated before it is pumped by pump 46a and thereafter processed, blockage problems are minimized.

Figure 6:
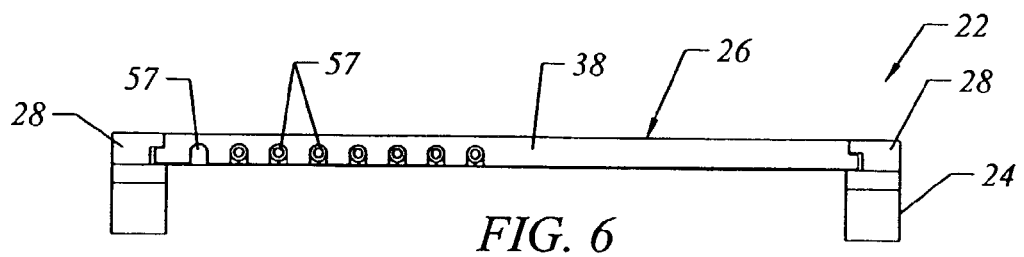
FIG. 6 is an end view of the cassette assembly of FIG. 5.

Cassette body 38 (FIG. 6) has a number of U-shaped channels 57 sized to receive the various lines 44, 52, 68, 76 and 94. The lines are maintained in position across openings 45, 48A, 80A, 90A and 96A and can be affixed within channels 57 using an adhesive. Therefore when roller assemblies 46, 54, and 72 engage their associated tubing segments 44A, 52A, 68A, the locations of tubing segments are accurately fixed to provide consistent flow rates. Affixing the tubing in channels 57 helps to ensure the correct tubing segment is engaged by the correct roller assembly and pinch valve plunger. The arrangement of the plungers (such as plungers 48, 80, 90, 96) and their associated solenoids, see FIGS. 2 and 8, in a staggered, two-dimensional array allows for the apparatus to be more compact and the disposable cassette 26 to be smaller and thus cost less.

The operations of the various components are controlled by a controller 58 housed within housing 4 and coupled to control panel 16 and a pressure sensor 60 as indicated by signal terminals P1, P2 and SP1–SP8. Controller 58 is a conventional microprocessor-based control system developed for blood processing systems and similar products. Controller 58 thus controls the actuation of blood pump roller assembly 46, anticoagulant pump roller assembly 54 and pinch valve plunger 48 according to the particular programming of controller 58 and pressure inputs from diaphragm-type pressure access ports 62, 64. These diaphragm-type pressure access ports permit accurate access to pressures within cassette 26, but do so without compromising the sterility of the system. The pressure measurements are made by using a pressure isolation device (not shown) at each pressure access port 62, 64. Each pressure isolation device includes a flexible diaphragm sealed on each side to a rigid enclosure or housing. The fluid to be measured flows on one side of the diaphragm. The other side of the diaphragm is exposed to a trapped air volume that communicates with a pressure transducer in pressure sensor 60 through access ports 62, 64 and associate pneumatic lines (not shown). The flexibility of the diaphragm ensures that the air pressure measured by the transducer equals the fluid pressure on the other side of the diaphragm.

An alternative approach is to allow the air side of the diaphragm of the pressure isolator to directly contact the flat face of a pressure transducer. The pressure sensor will then directly measure the fluid pressure on the other side of the diaphragm. Other pressure sensor devices may also be used.

Line 44 continues to a T coupling 66 at which line 44 splits into a recirculation loop 68. Recirculation loop 68 has a number of components along the loop. First along loop 68 is an optional whole blood filter 70 which, for example, uses a screen or pad or mat of fibrous material to trap leukocytes (white blood cells) and platelets by adhesion. An example of whole blood filter 70 is one made by Pall Corporation of East Hills, N.J., and as described in U.S. Pat. No. 4,985,153. Recirculation loop 68 also has a recirculation pump 72A along its length. A plasma separator 74, often referred to as a tangential flow separator, along loop 68 is used to remove plasma from the blood passing along loop 68, and directs the plasma through a plasma line 76 to a plasma bag 78. Plasma separator 74 is preferably a hollow fiber type of separator made for this application. A pinch valve 80A selectively seals off line 76 as discussed below. The recirculation of the blood through the recirculation loop 68 allows use of a plasma separator 74 which has significantly less fiber surface area than would be necessary if the blood was passed through it only a single time. Generally the fiber surface area of the separator can be reduced to only about one-third of what it would have to be in the absence of the recirculation loop 68. While providing the recirculating loop 68, recirculation or storage bag 12 (usually), and pump 72A requires a slightly higher capital cost than would be required in the absence of these components, the saving in cost of disposable plasma separators soon dwarfs this added capital expense. The way that the apparatus works is that the hematocrit (generally equal to the fraction of red blood cells) is increased significantly with the first pass through the plasma separator 74 and then increased again with each successive pass until the desired increase in hematocrit is obtained.

A thermoelectric cooler 82 extends from front panel 14, passes through a slot 83 in cassette body 36 and engages a segment 68B of loop 68 to selectively cool blood passing along loop 68. Thermoelectric cooler 82 includes a thermoelectric element and an attached heat sink that contacts tubing segment 68B for heat removal. A temperature measurement device (not shown) is used to measure and maintain, via feedback to a temperature controller, the desired tubing or heat sink temperature.

Recirculation loop 68 continues out beyond cassette 26 and connects to a recirculation storage bag 12 at a bag entrance 84 and at a bag exit 86. A pinch valve 90A selectively seals loop 68 between bag exit 86 and T coupling 66.

Recirculation pump 72A operates at a much higher pumping rate than blood pump 46A. As the blood recirculates along loop 68, plasma is removed by plasma separator 74 to increase the hematocrit of the recirculating blood. During these operations, pinch valves 80A and 90A are both open.

During normal blood collection procedures, blood pump 46A operates until a fixed volume, such as 450 ml, of blood has been withdrawn from the donor. It is important to ensure that blood pump 46A does not operate so fast as to cause the donor's veins to collapse or create other uncomfortable or dangerous situations. This can be achieved in part by controlling the rate of blood pump 46A and by monitoring the pressure at pressure access port 62.

An understanding of the flows involved may aid in an understanding of the technology involved and of the invention. As mentioned, the whole blood processing technique of the invention suitably uses recirculation through a hollow fiber plasma separator 74 so that a relatively low surface area hollow fiber plasma separator 74 can be used thereby keeping costs of disposables down. FIG. 2A illustrates one embodiment of the invention which utilizes the recirculation technique. Blood roller pump 46 can be used to extract blood from a donor at the maximum rate which will not collapse the donor's vein (venous pressure is normally about 0 to 20 mmHg). This serves to reduce the time the donor must be hooked up to the blood collection apparatus. If a sudden drop in pressure occurs, this indicates the pump rate is too high and the controller reduces it. The pressure drop through needle 40 and associated tubing 42 to pressure access port 62, just upstream of blood roller pump 46 is known/calculable ($\Delta P = Q1 \times R$ where Q1 is the blood flow rate and R is the resistance of needle 40 and tubing 42 upstream of pressure access port 62—somewhat of a function of the donor's hematocrit—the venous pressure, Pvenous is then equal to P1 (the pressure measured by pressure access port 62)+Q1×R). The feedback control scheme maintains the calculated Pvenous at about 0 to 20 mmHg by varying Q1. There is typically about a 10–50 mm drop through the optional whole blood filter 70 which is downstream of blood roller pump 46. A pressure access port 64 is located downstream of pressure access port 64 and has a pressure drop across it of typically 200–400 mm. The enriched red blood cell output from the hollow fiber plasma separator 74 is partially pumped by recirculation pump 72 between filter 70 and pressure access port 64 and then again through hollow fiber plasma separator 74. Recirculation is continued until the blood hematocrit is raised from the donor value, normally about 40%, to the desired value, normally about 80%. The flow through the recirculation pump is adjusted such that P2=K, where K is an empirically determined constant between 150 and 300 mmHg selected to maximize plasma flow without causing excessive hemolysis. P2 is the pressure measured by pressure measurer 64 and Q2 is the flow rate through the recirculation loop. The relationship among Q2, P2 and H2 is as follows:

$$Q2 = \frac{P2}{C(H2)}$$

where H2 is the mixed blood hematocrit entering the separator and C is a constant dependent upon separator design parameters and temperature. Then when H2 reaches 80%, a value of Q2 is reached that correlates with this hematocrit. When this occurs the recirculation process is stopped by the controller 58. The overall flow equation is Q1=Q2+Q3. Where Q1 is the output flow from the blood pump 46, Q2 is the flow out of the recirculating bag 12 and into separator 74, and Q3 is the flow of plasma out of separator 74 to the plasma collection bag 78. Flow rates Q1 and Q2 are controlled as described above via controller 58 which receives the various flow rate (pump speed) and pressure signals. Flow rate Q3 is not controlled directly and is dependent upon P2, separator design parameters and blood parameters.

A somewhat different parameter, RS, may be used as a control parameter, instead of P2, to control and optimize the recirculation process, that is to maximize waste flow and minimize hemolysis. RS is calculated as follows:

$$RS = C(H2) = \frac{P2}{Q2}$$

RS is therefore a calculated parameter that is proportional to H2 and is derived from the measurement of P2 and Q2. R2 is in effect the resistance to flow of hollow fiber separator 74.

When the desired volume of blood has been withdrawn from the donor, blood pump 46A and anticoagulant pump 54A stop operating. Recirculation pump 72A continues to operate until the desired hematocrit reaches, for example, 80%. The hematocrit is determined by measuring the resistance to flow within plasma separator 74. This resistance to flow is essentially the pressure sensed at pressure access port 64 divided by the flow rate through recirculation pump 72A. When the particular resistance value, corresponding to the desired hematocrit is reached, recirculation pump 72A stops pumping. Pinch valves 48A and 80A are then actuated to seal off lines 44 and 76. A red blood cell storage solution, such as Nutricel, obtainable from Pall Corporation, contained within a red blood cell bag 92 is then fluidly coupled to line 44 at a T coupling 98 by a line 94 by releasing pinch valve 96A. Blood pump 46A then is operated to pump the red blood cell storage solution from bag 92 through whole blood filter 70, plasma separator 74, and into recirculation bag 12. This not only flushes blood from that portion of loop 68, but also provides the blood within bag 12 with the necessary storage solution. Bag 12, containing the concentrated red blood cells and storage solution, and plasma bag 78, containing plasma, are then sealed off and removed from bag hanger assembly 8 for storage, use, or further processing. Cassette 26, bag 92 and 15, needle 40 and associated tubing and lines (shown only in FIG. 2A) are typically disposed of.

Figure 4:
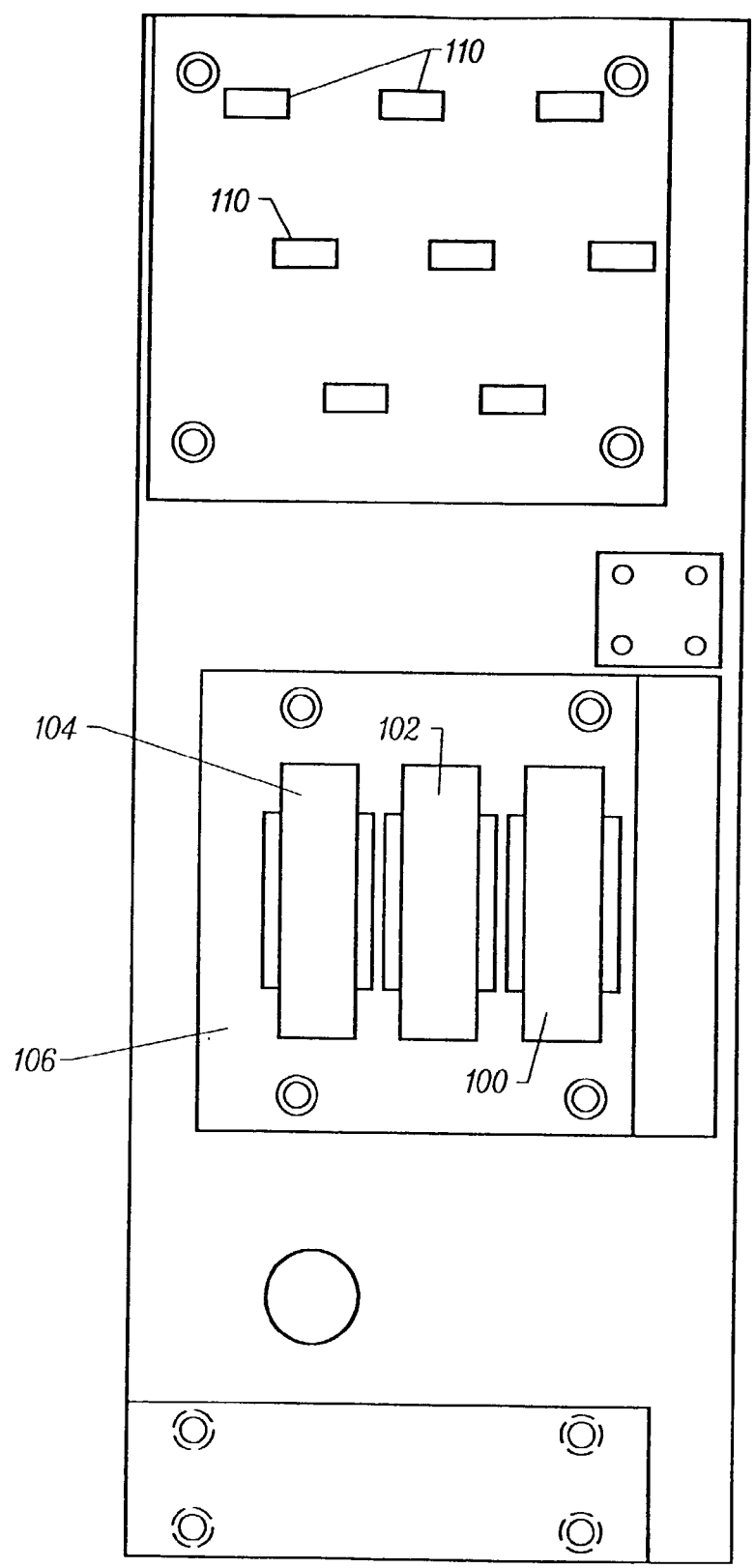
FIG. 4 is a view of the infacing side of the door of FIG. 3, that is the side facing the cassette assembly.

Tubing segments 44A, 52A, 68A are, as mentioned above, captured between roller assemblies 46, 54, 72 and arcuate roller tracks 100, 102, 104, respectively, formed in a block 106 of door 34 as shown in FIGS. 3 and 4. Door 34 also includes a block 108 having three rows of laterally extending raised elements 110, positioned opposite the eight pinch valve plungers shown in FIGS. 2, 4 and 8. In the present embodiment, only four of the eight pinch valve plungers, that is plungers 48, 80, 90 and 96, are used. The provision of additional pinch valve plungers and their associated plunger openings formed in body 38 of cassette 26 permits the invention to be used to conduct other types of blood processing procedures, two of which will be discussed below with reference to FIGS. 12 and 13. Similarly, additional pump roller assemblies, in addition to assemblies 46, 54, and 72, could be provided to accommodate additional pumps if needed. Note that the roller tracks 100, 102, 104 and the raised elements 110 can alternatively be provided on the cassette 26 in which case the through hole 45 is replaced by an indentation in the cassette 26.

Cassette 26 also includes up to four pressure couplers 112, one of which is shown in FIG. 3. Each pressure coupler 112 includes a pneumatic fitting 114 (see FIGS. 2 and 8) which engages a complementary pneumatic fitting 116 on front panel 14 of housing 4 when cassette assembly 26 is in the use position of FIG. 1. Pneumatic coupling 112 also includes a tube fitting 118. A flexible tube, not shown in any of the figures, extends from each tube fitting 118 to diaphragm-type pressure access ports 62, 64 (see FIGS. 2A and 5). This permits pressure in lines 44, 68 to be sensed and monitored by pressure sensor 60 in a non-invasive manner. Again, cassette 26 provides four pressure couplings, two more pressure couplings 112 than are needed for the embodiment of automatic blood collecting system 2. Doing so permits the same basic body 38 of cassette 26 to be used for a number of different blood processing systems. Providing extra pinch valve plungers and pneumatic fitting on front panel 14 permits the same basic housing 4, door 34 and cassette holder 24 to be used for a number of different blood processing systems as well.

Figure 9:
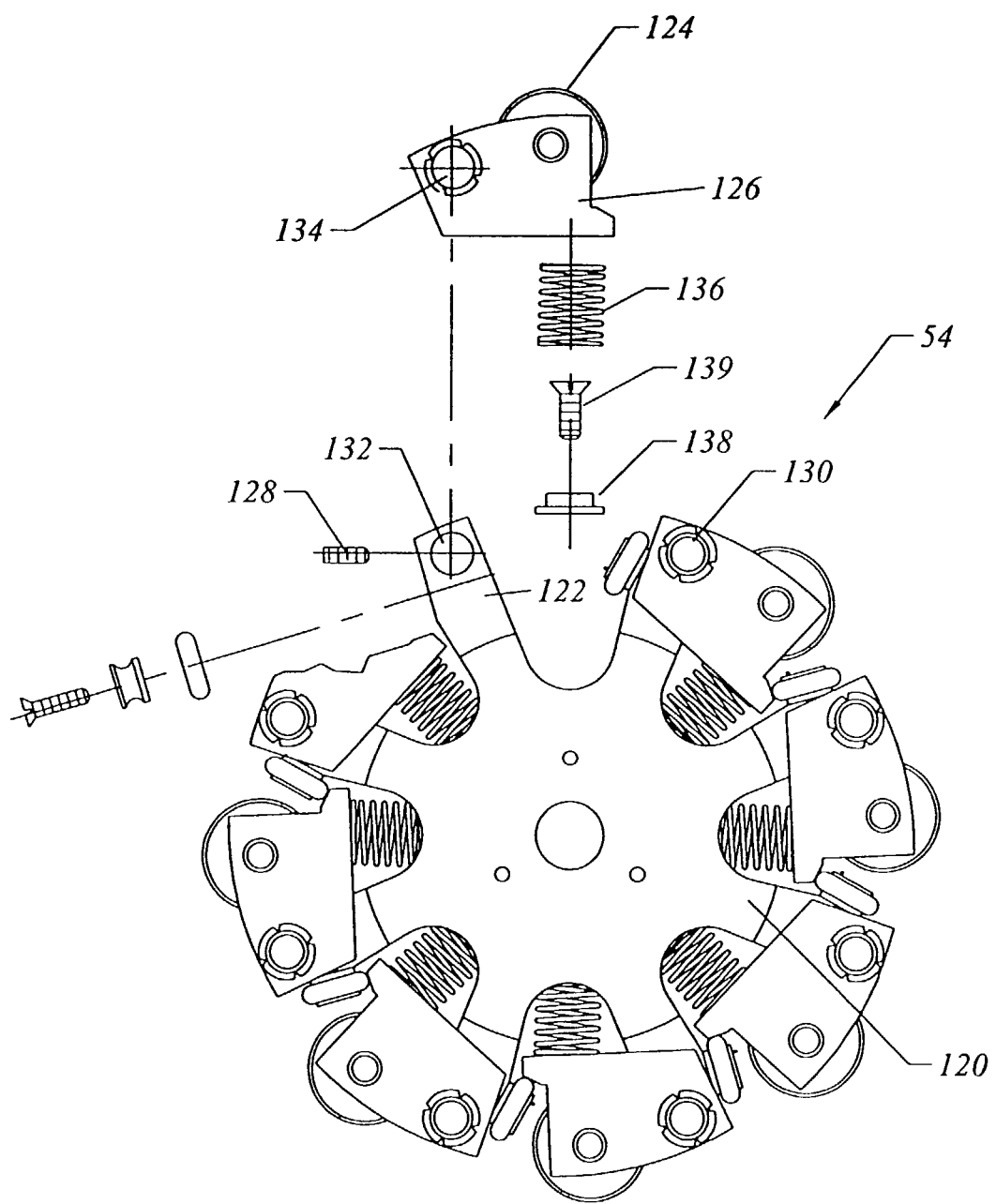
FIG. 9 is a partially exploded view of the center roller assembly of FIG. 8 illustrating the pivotal mounting of a roller.

FIG. 9 illustrates a partially exploded view of roller assembly 54. Roller assembly 46 includes a rotatable frame 120 having eight mounting arms 122. Each mounting arm 122 mounts a roller 124 to its outer end using a roller mount 126 pivotally mounted to the distal end of mounting arm 122. A set screw 128 secures a mounting pin 130 within coaxial bores 132, 134 formed in arm 122 and roller mount 126, respectively. Roller 126 is biased outwardly through the use of a compression spring 136 captured between frame 120 and roller mount 126. The inner end of spring 136 is maintained in place by being mounted over an annular spring guide 138, the spring guide being held in place by a screw 139. Instead of spring-biasing each roller 124 with a separate spring 136, each roller track 104 could be separately spring-biased against roller assemblies 46, 54, 72. Also, each roller assembly 46, 54, 72 could be separately biased against door 34. Of course a combination of biasing schemes could be used.

Figure 10:
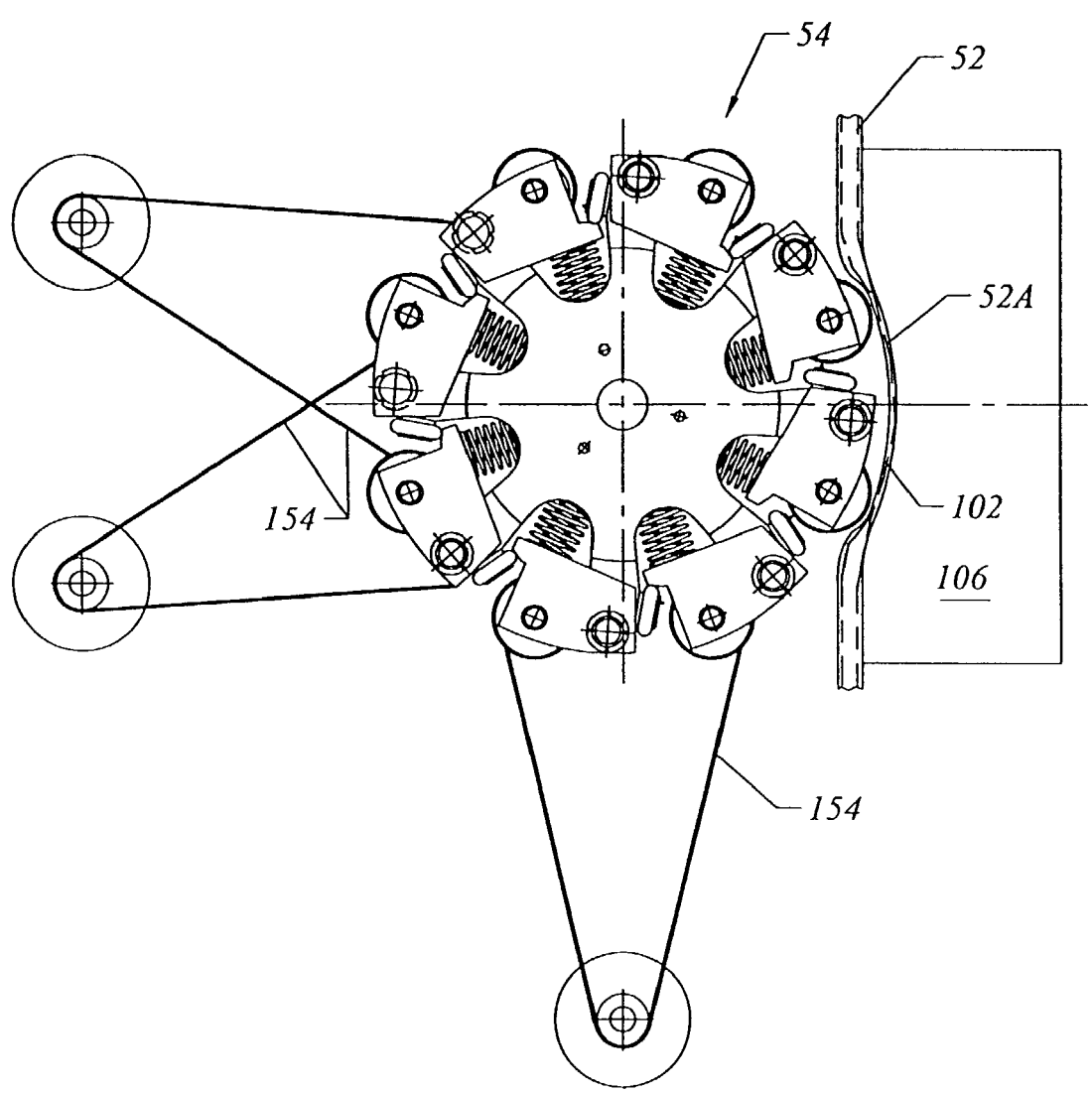
FIG. 10 shows the rollers of the center roller assembly of FIG. 8 engaging a tubing segment, the tubing segment captured between the rollers and an arcuate roller track of FIGS. 3 and 4, and showing the offset placement of two of the three drive motors for the three roller assemblies.
Figure 11:
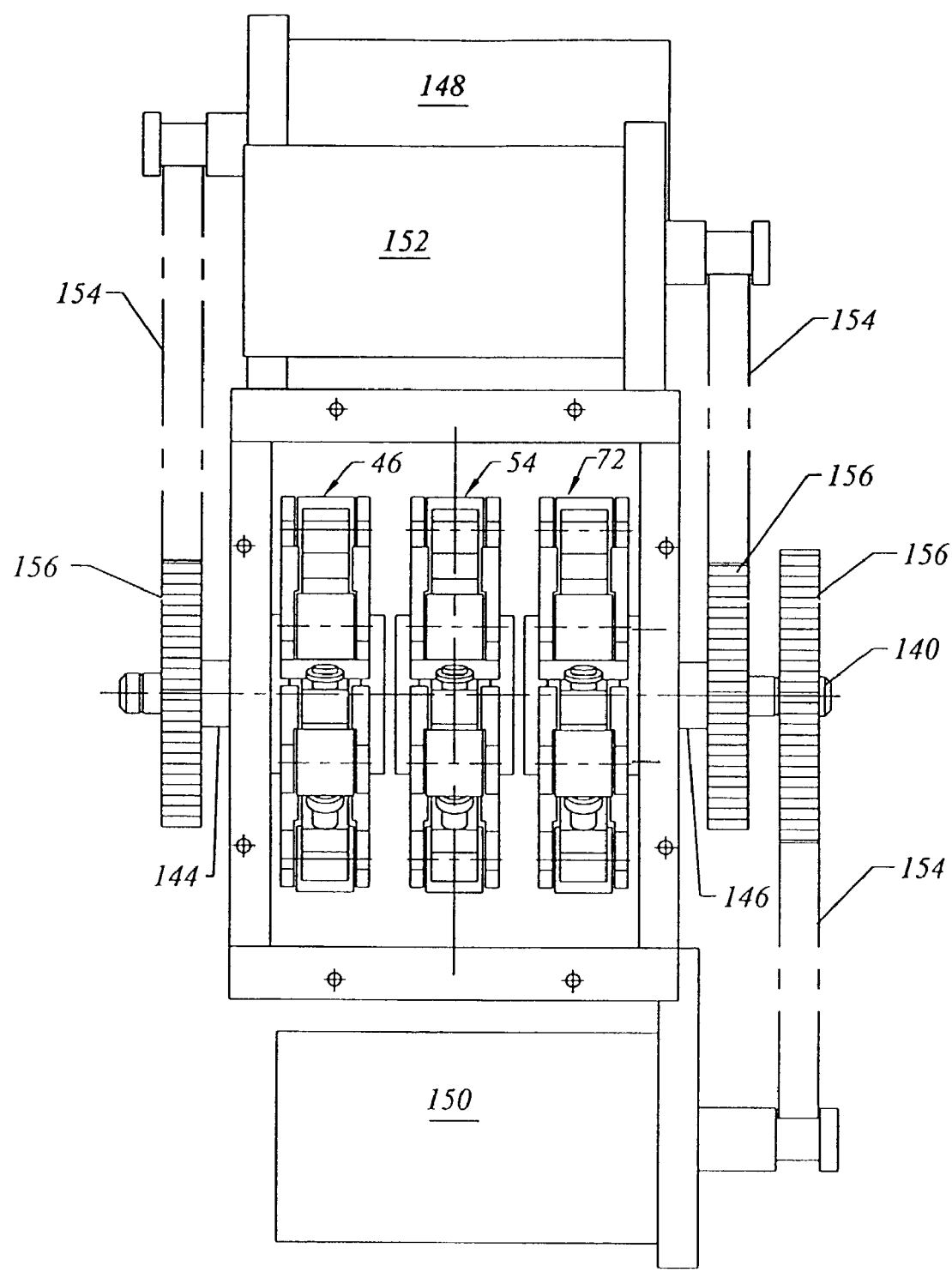
FIG. 11 illustrates the roller pump drive assembly including the three roller assemblies and three drive motors with the offset, overlapping orientation of the drive motors shown.
Figure 11A:
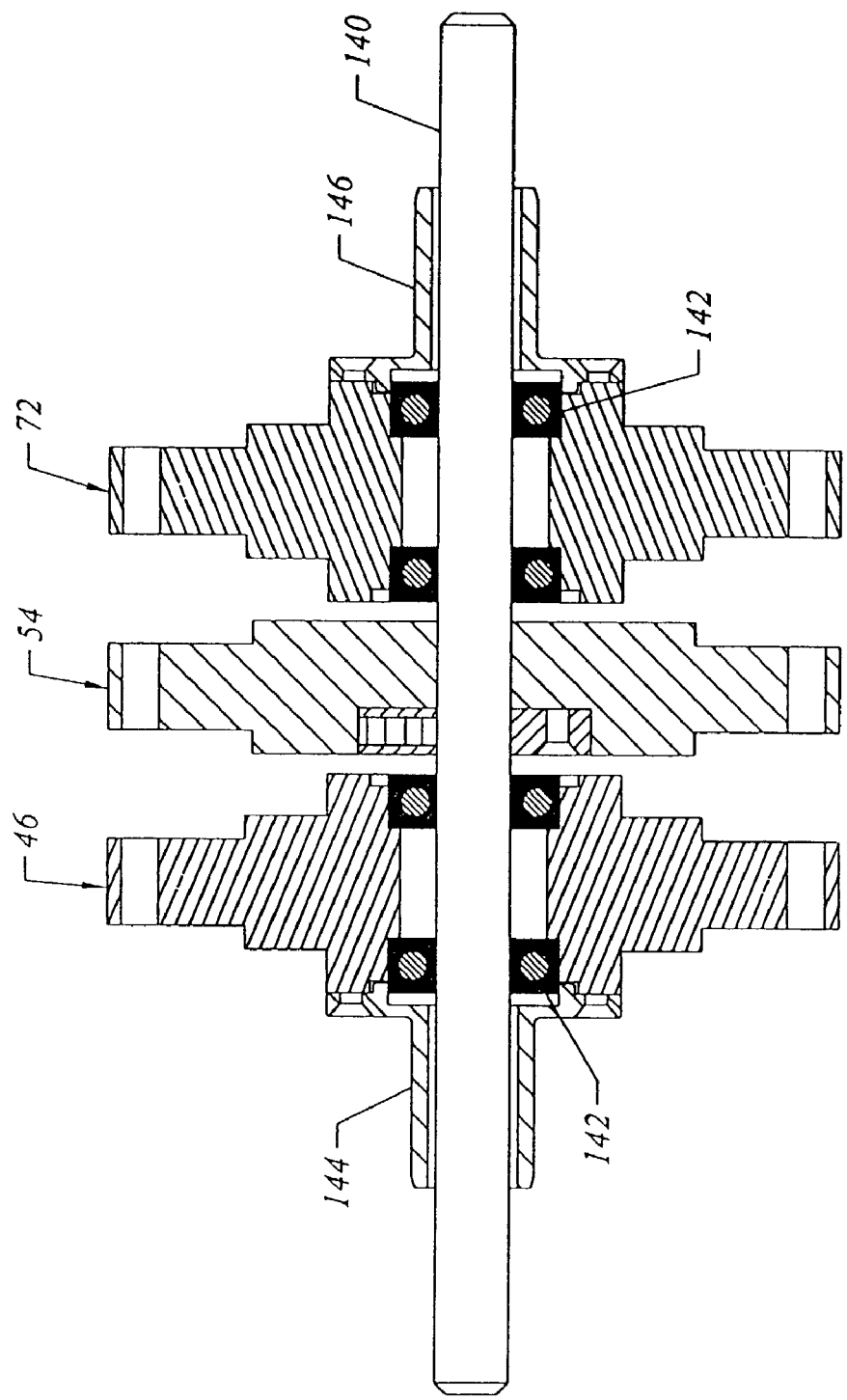
FIG. 11A is a simplified side cross-sectional view illustrating coaxial, nested drive shafts used to drive the roller assemblies.

Turning now to FIGS. 10, 11 and 11A, it is seen how all three roller assemblies 46, 54, and 72 have been made to be individually driven, but positioned at a very close axial spacing. FIG. 11A illustrates, in a somewhat schematic form, a main support shaft 140 which passes through and radially supports each of the roller assemblies. Roller assembly 54 is keyed to shaft 140 and thus is both supported by and is rotated by shaft 140. Roller assemblies 46 and 72 freely rotate on shaft 140 by virtue of the use of bearings 142.

Roller assemblies 46, 72 are secured to and driven by hollow drive shafts 144, 146 which are coaxial with and surround main drive shaft 140. FIGS. 10 and 11 illustrate the positioning of separate drive motors 148, 150, 152 which individually drive roller assemblies 46, 54, 72 through associated drive belts 154 and drive pulleys 156. Since all drive connections are axially located there are no gears or pulleys between the roller assemblies. Utilizing this type of mounting structure with the motors as close together as possible leads to an overall unit which is quite compact and minimizes cassette size.

Automatic blood collection system 2 is typically used to automatically collect a predetermined volume of blood from a donor, remove leukocytes and platelets from the collected blood and also remove a certain amount of plasma from the rest of the blood until a desired hematocrit is achieved. By using a recirculation loop and separator flow control in the loop to obtain the desired hematocrit, a much lower fiber surface area, and thus much less expensive, normally disposable, plasma separator can be used. This not only reduces the cost of collection of each unit of blood, it also reduces the size and bulk of the disposable cassette.

One aspect of the invention is the ability to test cassette 26 for leaks in a simple manner. Cassette 26 is preferably separate from cassette holder 24 during testing, typically by the manufacturer. At this point all tubes are open (not sealed by roller assemblies or pinch valve plungers). Each tube, except one, extending from the cassette is sealed. The one unsealed tube is coupled to a pressurized fluid source, such as compressed nitrogen, to pressurize the tubing and components of the cassette. While continuing to monitor the pressure in the cassette tubing, the tubing is removed from the pressurized fluid source. The pressure within the cassette tubing is then monitored to determine if there is an unacceptable drop in pressure over a chosen period of time. If the pressure drop is in excess of what is considered acceptable, the cassette is considered defective and removed for reworking, salvage or disposal. It is important for cassette 26 to be leak-free during use to ensure against contamination of the blood and to protect workers against exposure to harmful, and sometimes potentially deadly, blood products.

Prior to use, door 34 is released from front panel 14 through the use of a handle 160 carried by the door. This permits door 34 to be pivoted outwardly away from front panel 14 from the latched position of FIG. 1 to the released position of FIG. 3. Doing so also permits cassette holder 24 to pivot from its use position, parallel to panel 14, of FIG. 1 to its cassette replacement position of FIG. 3. This is preferably aided by the use of a spring (not shown) captured between the base of cassette holder 24 and front panel 14 to normally bias cassette assembly 22 to its cassette replacement position of FIG. 3.

As an alternative, cassette 26 can have alignment holes (or pins) which mate with pins (or holes) of the front panel 14. In this embodiment it is properly positioned by the hole/pin mating. Any desired structural method, a door, snap fasteners, bolts, etc., can be used to fasten the cassette 26 in the latched position.

Figure 5:
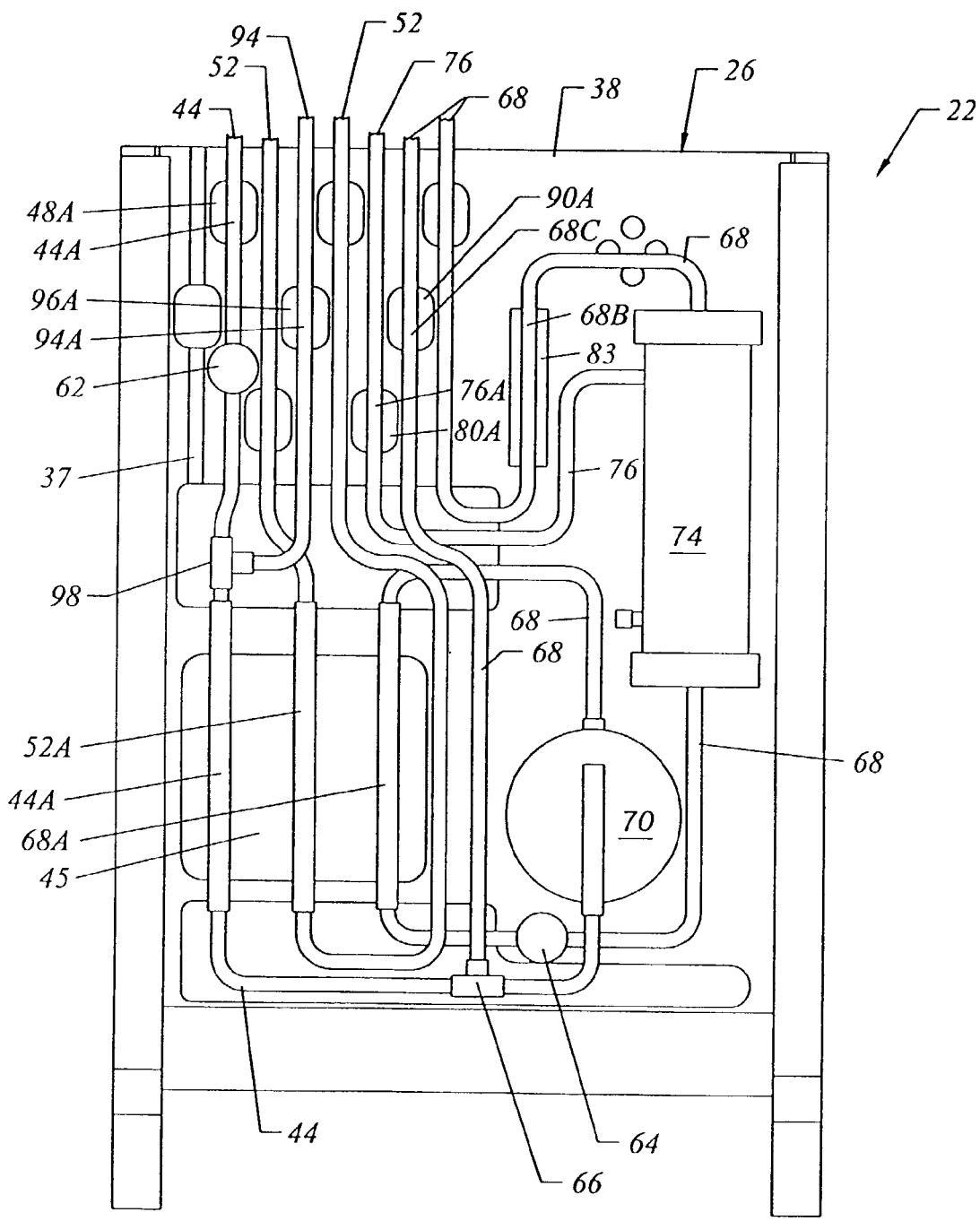
FIG. 5 illustrates the outfacing side of the cassette assembly of FIG. 3.

Cassette 26 and bags 12, 50, 78, and 92 come preconnected by tubing. The tubing connecting the various bags and cassette 26 is not shown in the figures, except for schematic FIG. 2A, for clarity. Bags 12, 50, 78, and 92 are hung on bag hanger assembly 8 and cassette 26 is inserted between side rails 28 of cassette holder 24 until fully housed within cassette holder 24 as shown in FIGS. 3 and 5.

Mechanical bag manipulator 10 is used to manipulate recirculation bag 12 during the operation of system 2.

Once the various components are in place, controller 58 is set using input pads/buttons 18. For example, one of the pads/buttons can be used to scroll through a number of different blood processing procedures stored in the controller. When the automatic blood collection system procedure is displayed, that can be selected. The volume of blood to be collected can be preset or it can be changed by the user. A bar code on the cassette can be used to identify the correct blood processing procedure for that cassette. A bar code reader (not shown) on the system implements that procedure. Once the various input data are entered, the tubing is primed with fluid (normally anticoagulant solution), needle 40 is inserted into a vein of the donor and system 2 is actuated. Initially, pinch valve plunger 96 is extended to seal line 94 while the remaining pinch valve plungers are retracted. Blood pump 46A begins operating to pump blood from the donor and into recirculation loop 68. Recirculation pump 72A, which runs at a higher pump rate than blood pump 46A, forces the blood through recirculation loop 68 whereby leukocytes and platelets are removed, if desired, by whole blood filter 70 (filter 70 is optional) and plasma is removed by plasma separator 74. Processed blood is then delivered to recirculation bag 12. Because pump 72A is pumping faster than pump 46A, blood from pump 46A and blood from recirculation bag 86 is pumped through recirculation loop 68. This permits the blood collected in bag 12 to have its hematocrit raised. During the operation of blood pump 46A, anticoagulant pump 54A also operates to direct a flow of anticoagulant from anticoagulant bag 50, the flow rate of the anticoagulant being proportional to the flow rate of the blood being drawn from the donor.

When it is determined that blood is no longer to be drawn from the donor, which can occur automatically when a predetermined volume of blood has been pumped or, for example, when a certain time period has elapsed, or upon manual intervention, blood pump 46A and anticoagulant pump 54A are halted and pinch valve plunger 48 is extended to seal line 44 upstream of port 62. If necessary to achieve the proper hematocrit, recirculation pump 72A can continue to recirculate blood through recirculation loop 68. Once the desired hematocrit has been achieved, which is determined by sensing the resistance to flow through plasma separator 74, pump 72A is halted, pinch valve plunger 80 is extended and pinch valve plunger 96 is retracted. At this point, blood pump 46A is again actuated to pump storage solution from bag 92 or anticoagulant from bag 50 through the initial portion of loop 68 and into recirculation bag 12 thus flushing this portion of loop 68 as well as providing bag 12 with the blood storage solution. Once the storage solution has been pumped into the recirculation bag, pump 46A is stopped and pump 46A is reversed causing the concentrated red blood cells and storage solution in recirculation bag 12 to be pumped from bag 12, along loop 68, through line 94 and into bag 92. Pump 46A is then stopped. At this point, bag 92 and bag 78 can be removed from system 2, typically by first clamping off and sealing the tubes extending to the bags and then severing the tubes between the seals. Handle 60 is then manipulated to open door 34. This permits cassette 26 to be removed from cassette holder 24 so cassette 26, needle 40, anticoagulant bag 50, recirculation bag 12 and associated tubing can be disposed of.

Figure 12:
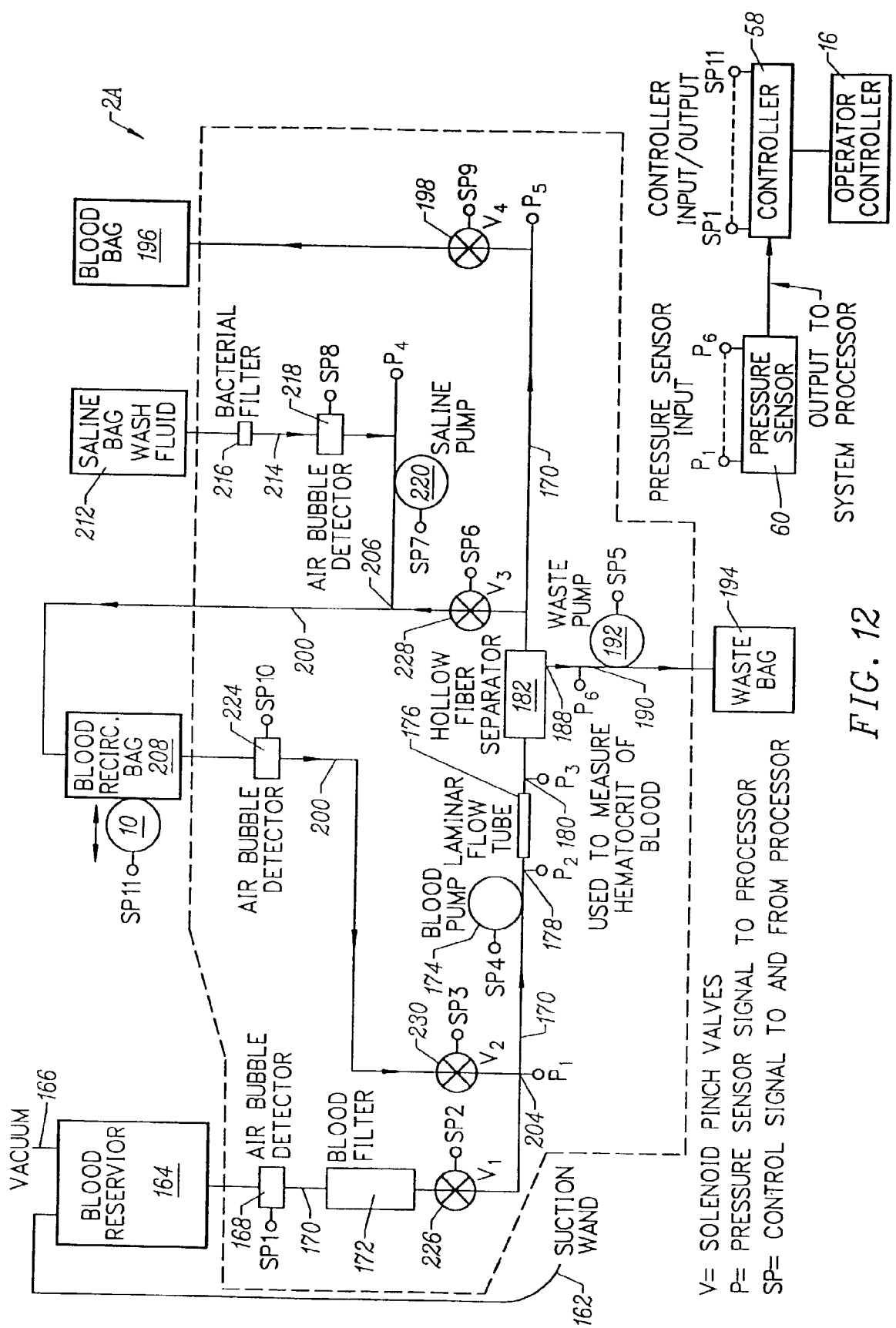
FIG. 12 is a schematic illustration of an autotransfusion system made according to the invention.

FIG. 12 illustrates, in schematic form, an alternative embodiment of the invention of FIG. 2A with like features referred to with like reference numerals. Autotransfusion system 2A provides certain advantages, including completely automatic operation with simple setup. There is negligible red blood cell loss, low hemolysis and low loss of platelets to waste bag 194. System 2 is designed to reduce the blood volume along the various lines and within the various blood processing components to facilitate purging. As with the embodiment of FIG. 2A, there are no blood attachments to make or break, and the system is a completely closed system. By eliminating the use of centrifugal bowl separation devices, potentially leaky centrifugal bowl seals are eliminated. Also, as with the embodiment of FIG. 2A, system 2A is fail safe in that failure modes, such as a full or empty bag, can be quickly detected and automatically responded to by virtue of the various pressure measurements and ultrasonic sensor air bubble detection.

Blood, along with entrapped air, diluent liquid, damaged cells, cellular debris, and particulate debris, is suctioned from the surgical wound site by a suction wand 162. Conventional methods of anticoagulation, not shown, are used. For example, a manually controlled heparin or CPD drip can be provided at suction wand 162. The red blood cell containing liquid flowing from suction wand 162 passes into a blood reservoir 164, which hangs from bag hanger assembly 8. Blood reservoir 164 is supplied with a vacuum at vacuum port 166 to create the necessary suction at suction wand 162.

Blood reservoir 164 may be a conventional cardiotomy reservoir having a built-in blood filter to remove particulate debris. Blood reservoir 164 may contain a quantity of blood at the time it is coupled to the cassette. The commitment of the disposable cassette is usually not made until the user believes there will be enough blood of sufficiently good quality to justify conducting the processing procedure. The blood-containing liquid accumulates in blood reservoir 164 until a sufficient amount of blood is obtained to justify processing. The blood-containing liquid from the blood reservoir 164 then passes into the cassette, past an air bubble detector 168, along a blood entrance line 170. A blood filter 172 is located along line 170 and is used to remove particulate debris and some of the entrapped air. Blood filter 172 will not be needed when blood reservoir 164 is a conventional cardiotomy bag with its built-in blood filter. A blood pump 174, positioned further down line 170, initially operates at a fairly low flow rate, such as about 200 ml/min. to 500 ml/min., and turns off if air bubble detector 168 detects air bubbles, indicating a low or empty blood reservoir. The blood-containing liquid is pumped through a laminar flow tube 176 positioned along line 170. Laminar flow tube 176 is used to measure the hematocrit of the blood-containing liquid by the use of a pair of pressure access ports 178, 180 on either side laminar flow tube 176. Hematocrit can also be measured by, for example, the use of a calibrated optical detector for the direct measurement of hematocrit or through the use of pressure differential measurement across a hollow fiber separator 182 or by use of the inlet pressure to the hollow fiber separator.

The blood containing liquid collected from a wound site often contains substances which should not be reinfused back into the patient and its hematocrit is generally quite low due to dilution, typically from about 5% to about 40% and subject to great variation. For example, such substances as particulates (e.g., tissue fragments and thrombus), commonly removed by blood filter 172, and wash liquid, other bodily fluids and cellular debris which is smaller than the pore size of the fiber surface (leached blood cells) are removed by a hollow fiber separator 182 along line 170. Hollow fiber separator 182 has an inlet 184 and an outlet 186 along line 170 and waste outlet 188 coupled to a waste line 190. Waste line 190 has a waste pump 192 which pumps liquid, such as non-blood fluids along with plasma and particulate waste which passes through the fiber pores, along waste line 190 to a waste bag 194, bag 194 also being supported by bag hanger 8. A pinch valve 198 along that portion of line 170 which couples exit 186 with a blood bag 196, and a pinch valve 230, located along a recirculation line 200 near a T coupling 204 along line 170, are closed during this initial pumping. Blood flows from separator 182 through recirculation line 200 and to blood recirculation bag 210. Line 200 extends from a T coupling 202 near outlet 186 to T coupling 204 between blood filter 172 and blood pump 174.

Pinch valve 226, along line 170 between blood filter 172 and T coupling 204, and pinch valve 228, along line 200 between T couplings 202 and 206, remain open during this initial operation of the system. Blood is pumped along line 200 and into a blood recirculation bag 210, having an entrance 208 and an exit 222, until a desired volume, such as 200 ml, is collected in bag 210 or until air bubble detector 168 indicates blood reservoir 164 is empty. This ends the blood collection step.

To begin the blood concentration step, pinch valve 230 is opened and pinch valve 226 is closed. Blood is recirculated through loop 200 and hollow fiber separator 182 to raise the hematocrit up to any desired value such as, for example, 45%. The control of the concentration step is the same as that used for whole blood collection. One reason system 2A is operated with a concentration step followed by a wash step is because the hematocrit of the blood in reservoir 164 can have a hematocrit of, for example, 5% to 40%. The wash process is much more effective if done at a higher hematocrit, for example, 45% or more: less saline is used and washing takes less time.

Saline pump 220, along saline line 214, is used to supply saline or other wash fluid to recirculation line 200 at a T coupling 206 between T coupling 202 and the inlet 208 of blood recirculation bag 210 during the blood washing step. A saline bag 212, supported bag hanger 8, contains the supply of saline. Saline line 214 includes an air bubble detector 218 which is monitored so that operation pump 220 can be halted when the supply of saline wash fluid is low or exhausted.

Blood recirculation bag 210 is housed within mechanical bag manipulator 10 to permit the contents of bag 210, that is the cleaned blood and saline wash fluid, to be thoroughly mixed within the bag. Bag manipulator 10 is designed to knead, punch, shake or otherwise manipulate bag 210. Blood recirculation bag 210 has an outlet 222 through which the blood and saline wash fluid pass through the remainder of segment 200. An air bubble detector 224 is used along line 200 to indicate when bag 210 is empty. Both saline pump 22 and blood pump 174 operate while the blood is being washed. Saline is added at about the same rate as waste fluid is removed from separator 182 by pump 192. Bag manipulator 10 operates during both the concentration mode, during which the hematocrit is raised to about 45%, and during the washing mode, during which saline or other wash solutions are pumped by saline pump 226.

At the end of the wash step, the hematocrit of the blood is preferably about 55%. Pinch valve 228 is then closed, pinch valve 198 is opened and saline pump 220 is turned off so that the washed blood is pumped by pump 174 from bag 210 into bag 196.

After the blood has been pumped into blood bag 196, pinch valves 198 and 230 are closed, pinch valves 226 and 278 are opened, blood pump 174 is operated and air bubble detector 168 is monitored to determine if blood reservoir 164 has blood in it. If it does, the process is repeated.

When air bubble detector 168 detects air bubbles, blood pump 174 stops and reverses direction and saline pump 220 is operated to pump the blood in the lines and saline back through the lines into blood reservoir 164. This is done to eliminate air in the lines and components because air can interfere with proper operation of some components, such as separator 182, and can cause hemolysis. Unless the operator either turns system 2A off or places system 2A in a pause mode, controller 58 starts pump 174 after a waiting period, for example 15 or 20 seconds, to determine if blood reservoir 164 has blood in it.

System 2A is typically operated in three different modes. During the standard mode about 90–92% of the free plasma hemoglobin, anticoagulant and other waste material are removed by operating the wash cycle (during which saline pump 220 is pumping a wash solution into the recirculating blood) for a predetermined period of time, such as about 2 to 5 minutes. The second mode is called the orthopedic mode; the wash cycle is operated for a longer period of time and a greater, specific consumption of saline solution to get about a 98% removal of the waste material. This higher waste material removal is needed in order to wash out the higher initial levels of free plasma hemoglobin and small particulate debris. The third mode is called the fast mode. During the fast mode the washing step is eliminated so that saline pump 220 is not operated; the blood is passed through separator 182 to raise the hematocrit to about 40% and remove some amount of waste material. Once the desired hematocrit level is reached, the concentrated blood is pumped into blood bag 196. The fast mode is suitable for surgical procedures that result in loss of relatively clean blood.

Figure 13:
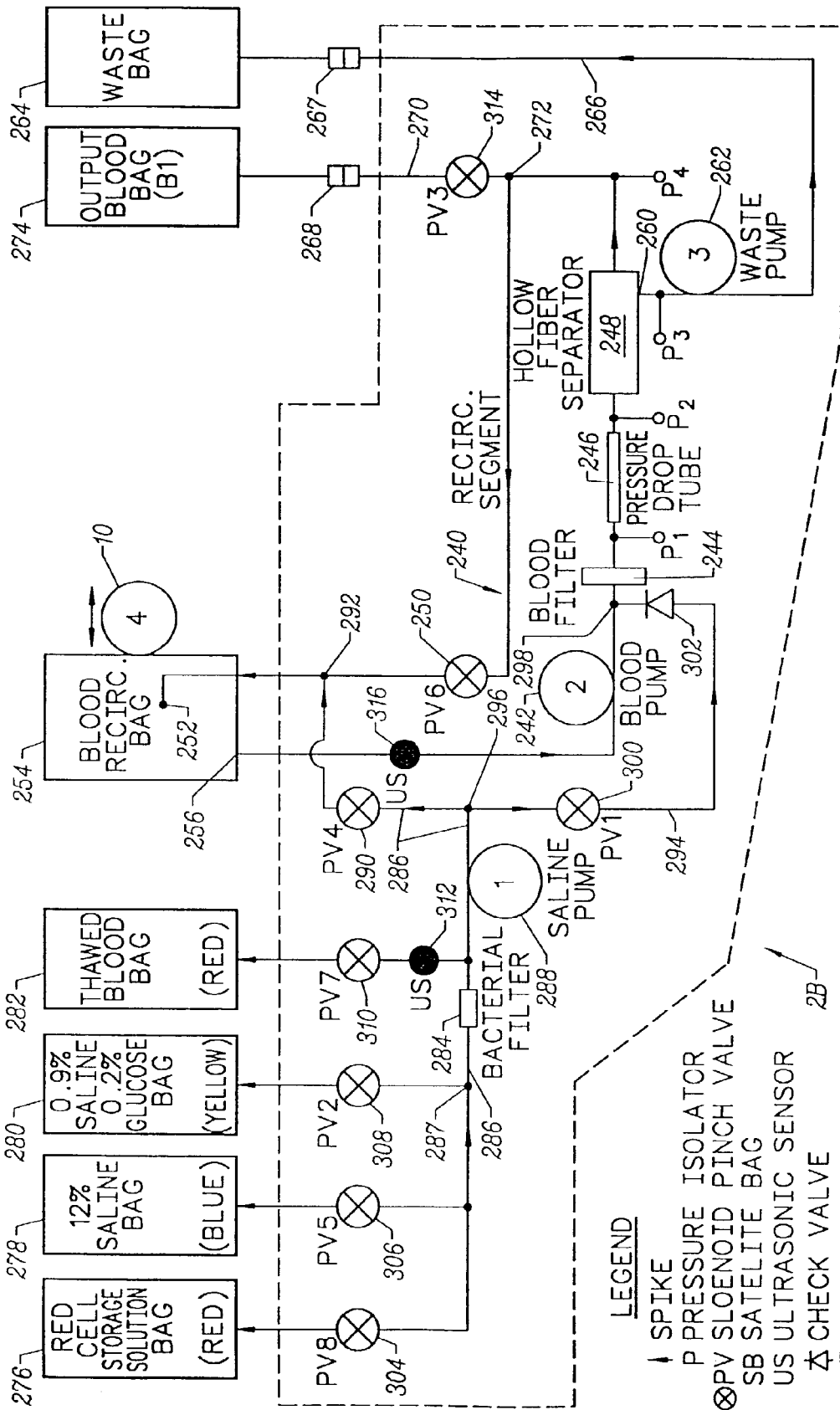
FIG. 13 is a schematic illustration of a thawed blood processing system made according to the invention.

Thawed blood processing system 2B is illustrated in schematic form in FIG. 13. System 2B is intended to remove glycerol and free plasma hemoglobin from thawed, previously frozen blood. The use of the invention enables the storage of deglycerized red cells on the order of a few to several weeks because the system uses a closed and sterile disposable cassette. This is a major advantage over other thawed blood processing systems which use centrifugal separators with rotating seals, which have not been considered closed and sterile by the FDA. Thus, in those situations the deglycerized red cells have a maximum storage of only twenty-four hours, a major disadvantage.

Thawed blood processing system 2B includes broadly two major steps. The first step is the predilution step where saline is added to the thawed blood. The second step is the wash process in which a recirculation loop is used to wash free plasma hemoglobin and other waste material from the thawed blood.

As in the earlier embodiments of FIGS. 2A and 12, the termination of lines extending out from the cassette are indicated by dashed lines in FIG. 13. System 2B includes a recirculation loop 240 having a number of blood processing components along the loop. Specifically, loop 240 has a blood pump 242 which pumps blood along loop through a blood filter 244, through a pressure drop tube 246, through a hollow fiber separator 248, past a pinch valve 250, and into an inlet 252 of a blood recirculation bag 254. Bag 254 is housed within and mechanically manipulated by mechanical bag manipulator 10. Blood recirculation bag 254 has an outlet 256 fluidly coupled to blood pump 242 through an ultrasonic sensor 258. Sensor 258 is used to determine when fluid is flowing past the sensor along line 240. As with the embodiment of FIG. 12, the hematocrit of the fluid entering hollow fiber separator 248 is determined with reference to the pressure drop taken on either side of the pressure drop tube 246.

Hollow fiber separator 248 has a waste outlet 260 by which waste, typically a saline solution containing free plasma hemoglobin and glycerol, is removed from the fluid passing through the separator by pumping by a waste pump 262 into a waste bag 264 through a waste line 266. A blood outlet line 270 is connected to recirculation loop 240 at a T coupling 272 between hollow fiber separator 248 and pinch valve 250. Line 270 continues out past the cassette and is coupled to a blood outlet bag 274.

A red cell storage solution bag 276, a 12% saline bag 278, a 0.9% saline/0.2% glucose bag 280 and a thawed blood bag 282, are all supported by bag hanger assembly 8. The various lines coupled to bags 276, 278 and 280 all join together and flow into a saline pump line 286 at connection 287. A bacterial filter 284 is positioned along saline pump line 286 upstream of a saline pump 288. Saline pump 288 pumps fluid along saline pump line 286, past a pinch valve 290 and to a T coupling 292 along recirculation loop 240.

The cassette also includes a saline line 294 connected at either end to positions 296, 298 along lines 286, 240. A pinch valve 300 and a check valve 302 are used along purge line 294 to permit saline to be initially pumped through recirculation loop 240 from position 298, through blood filter 244, pressure drop tube 246, hollow fiber separator 248 and into blood recirculation bag 254 when system 2B is first started. This eliminates air within the lines to improve system performance and help prevent damage to the red blood cells passing through the line. Pinch valves 304, 306, 308 and 310 control the flow of fluid from bags 276, 278, 280 and 282.

Initially system 2B has all of its pinch valves closed except for pinch valves 310, 290, and 250. This permits thawed blood from thawed blood bag to be pumped by saline pump 288 from thawed blood bag 282 through saline pump line 286, into recirculation loop 240 and into blood recirculation bag 254. An ultrasonic sensor 312, positioned along a line 313 connecting thawed blood bag 282 to line 286, is used to sense when thawed blood bag 282 is empty. When this occurs, saline pump 288 is automatically stopped by the controller. Next, pinch valve 310 closes and pinch valve 306 opens to permit a predetermined amount, such as 50 ml., of 12% saline from bag 278 to be pumped through line 286 into blood recirculation bag 254 while the bag is being manipulated or shaken by manipulator 10 to ensure that the saline and thawed blood are thoroughly mixed. Contact of the thawed blood with the saline helps to shrink the red blood cells and force the glycerin out of the red blood cells. An equilibration time of about 3 minutes follows pumping of the 12% saline into bag 254; during this time saline pump 288 is off but bag manipulator 10 continues to manipulate bag 254. Saline pump 288 is operated to permit saline from bag 267 to pass into recirculation loop 240 to help remove most of the air from the recirculation loop. Pinch valves 306, 300, and 250 are open during air removal. Pinch valve 306 is closed and pinch valve 308 is opened so that saline pump 288 can be actuated to pump the saline/glucose mixture in bag 280 into bag 254. A fixed volume, such as 250 ml, of saline/glucose is pumped into bag 254 at a fixed flow rate while bag 254 is being manipulated by manipulator 10. Pinch valve 308 is then closed and saline pump 288 stops operating for a second equilibration period while manipulator 10 continues to manipulate or shake bag 254.

After this initial mixing process, the wash process of the thawed blood, saline and glucose mixture in bag 254 is begun. During the wash process pinch valve 308, 290 and 250 are opened while the other pinch valves are closed. The initial wash process occurs through the action saline pump 288 pumping the saline/glucose mixture into loop 240 and blood pump 242 pumping the fluid mixture in bag 254 through recirculation loop 240 so that waste, primarily free plasma hemoglobin, glycerol and a saline solution, is removed from the loop by hollow fiber separator 248 and pumped into waste bag 264 by waste pump 262. When the blood is considered washed, such as after a predetermined period of time, saline pump 288 is stopped, pinch valve 308 is closed and blood pump 242 and waste pump 262 continue to operate. This process is complete when a total volume of perhaps 800 ml of saline has been consumed. Then pinch valve 250 is closed, pinch valve 314 is opened and waste pump 262 is stopped which permits pump 242 to pump the washed blood at the desired hematocrit into blood outlet bag 274. A purging of red cells from separator 248 takes place by operating saline pump 288 to pump a volume of saline into recirculation bag 254 and then operating blood pump 242 to pump this saline through the separator, pushing residual red cells ahead of it into bag 274. Bag 274 can be separated from system 2B by pinching, sealing and cutting the tubing attached to the blood outlet bag.

During the washing step it is desirable to maintain a fixed pressure at the inlet of separator 248 by varying the operating speeds and flows of the waste pump and saline pump. This causes the saline flow rate to be lower and the waste flow rate to be higher when the hematocrit is lower. Doing so maintains the separator inlet hematocrit at an essentially fixed value and achieves consistent system and process performance.

The systems of FIGS. 14–17, described below, illustrate various structure for attaching the various bags to the cassettes. Some bags come pre-attached to the cassette, such as bags 12, 404, 404A of FIG. 17. This is indicated in FIGS. 14–17 by a plain, direct connection to the cassette. Break valves are used when fluid-filled bags are pre-attached to the cassette; this keeps the contents in the bags until operation of the system is to begin. Two common ways to make non-sterile connections to fluid-containing bags are through the use of spikes and Luer connectors; bacterial filters for the fluids are preferably used in these situations.

Figure 14:
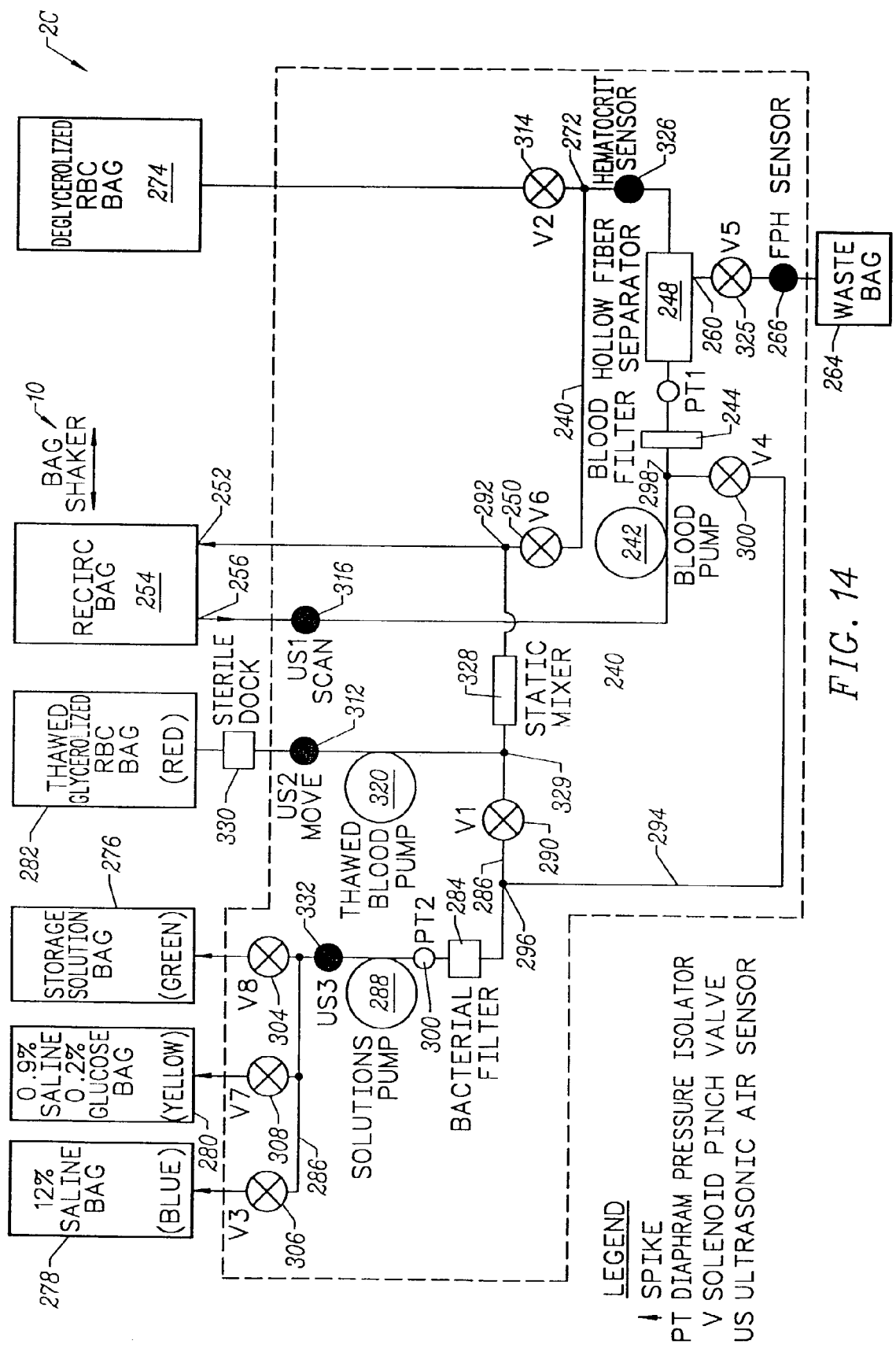
FIG. 14 illustrates an alternative embodiment of the thawed blood processing system of FIG. 13.

FIG. 14 is directed to an alternative embodiment of the thawed processing system 2B of FIG. 13 with like components referred to by like reference numerals. The primary differences between system 2B of FIG. 13 and system 2C of FIG. 14 are as follows. A thawed blood pump 320 is used along a line 322 extending from the thawed blood (glycerolized red blood cell) bag 282 to line 286 just downstream of solenoid pinch valve 290. Also, waste pump 262 has been eliminated from along line 266. It has been found that the separator 248 inlet pressure is sufficient to allow the waste to collect in waste bag 264 to eliminate the need for waste pump 262. The blood pump 242 flow rate is controlled to achieve an optimal value of separator inlet pressure PT1 to obtain high blood flow rates and low levels of free plasma hemoglobin or low levels of hemolysis. The free plasma hemoglobin (FPH) sensor 324, positioned between pinch valve 325 and waste bag 264, is used to measure the level of FPH in the waste line, to monitor this value in a digital display, to warn when it is too high at the end of the process, or to terminate the wash process when a satisfactory low level of FPH has been reached.

Pressure drop tube 246, pressure isolator P2 and pressure isolator P4 in a FIG. 13 embodiment has been eliminated and replaced by a hematocrit sensor 326 which senses the hematocrit by optical means by using light transmission or light scattering at specific wavelengths. Pressure isolator PT1 of FIG. 14, which corresponds to pressure isolator P1 of FIG. 13, is used to measure separator inlet pressure in order to control blood pump 242 flow rate at optimal values according to a control algorithm and may be used in conjunction with or in replacement of the hematocrit sensor 326 for this purpose. A static mixer 328 is used along line 286 between the intersection 329 of lines 322 and 286 and intersection 292. Static mixer 328 is used to help ensure the proper mixing of the thawed blood from bag 282 with the 12% saline solution from bag 278. A sterile dock 330 positioned along line 322 between ultrasonic sensor 312 and bag 282 is used to perform a sterile attachment of the thawed blood bag 282 to the sterile disposable set during the setup of the disposable set. An ultrasonic sensor 332 is positioned just upstream from pump 288 and is used to provide an indication to the controller when bubbles appear in the line as indicating the source of the particular solution being pumped has been effectively exhausted. The operation of system 2C is substantially the same as the operation of system 2B of FIG. 13 with the slight modifications discussed above.

The process carried out by FIG. 14 is essentially identical to that of FIG. 13. Early in the process there is a priming step that adds 0.9% saline solution from the bag 280 to the hollow fiber separator 248 and the blood filter 244 to remove air and replace it with saline; most of that saline ends up in the waste bag and replacing air in both devices. The 12% saline solution from bag 278 is added by using the solutions pump 288; it flows through static mixer 328 simultaneously with the thawed glycerolized RBCs pumped out of bag 282 by thawed blood pump 320 so the flow streams of the 12% saline and the RBCs mix in junction 329 and also in static mixer 328 before they flow into recirculation bag 254. That process is complete when all of the thawed glycerolized RBCs are removed from bag 282. Recirculation bag 254 is shaken during the addition of 12% saline. Then there is about a three minute equilibration time when bag 254 is shaken but nothing else is happening. Then a certain quantity of the 0.9% saline 0.2% glucose solution from bag 280 is added by the solutions pump 288 through the static mixer 328 and into the recirculation bag 254 where it mixes in the bag with the blood. At that point the recirculation process begins. The blood pump 242 begins to pump blood through the hollow fiber separator and back into the recirculation bag 254 which is shaken to accomplish mixing and maintain a homogeneous mix in the recirculation bag. The wash process that occurs is the concentration of blood to a higher hematocrit through the hollow fiber separator so that the hematocrit level for blood exiting the separator is raised. Then saline is added at point 272 using the solutions pump 288 to pump the 0.9% saline 0.2% glucose to point 272, the objective being to replace waste that has been removed by the hollow fiber separator 248 with an equivalent flow of saline, thus keeping the hematocrit in the recirculation bag 254 constant. This wash process is the same as that performed in FIG. 13 and proceeds for several minutes, during which time about 1500 ml saline are consumed and a similar amount of waste is produced. At that point the washing is complete; glycerol has been removed from the blood as has FPH. (System 2C could also be used to remove other compounds, such as viral inactivation compounds, from blood.) The blood pump 248 is used to pump blood out of the recirculation bag 254 into the deglycerolized RBC bag 274. Solutions from one or both of bags 276, 280 are added using the solutions pump 288 to the recirculation bag 254 purging red cells from separator 248 and then that is pumped out of the recirculation bag with blood pump 242 into the deglycerolized RBC bag 274 to add a storage solution to red cells that have been previously concentrated by the wash process up to a fairly high hematocrit.

Figure 15:
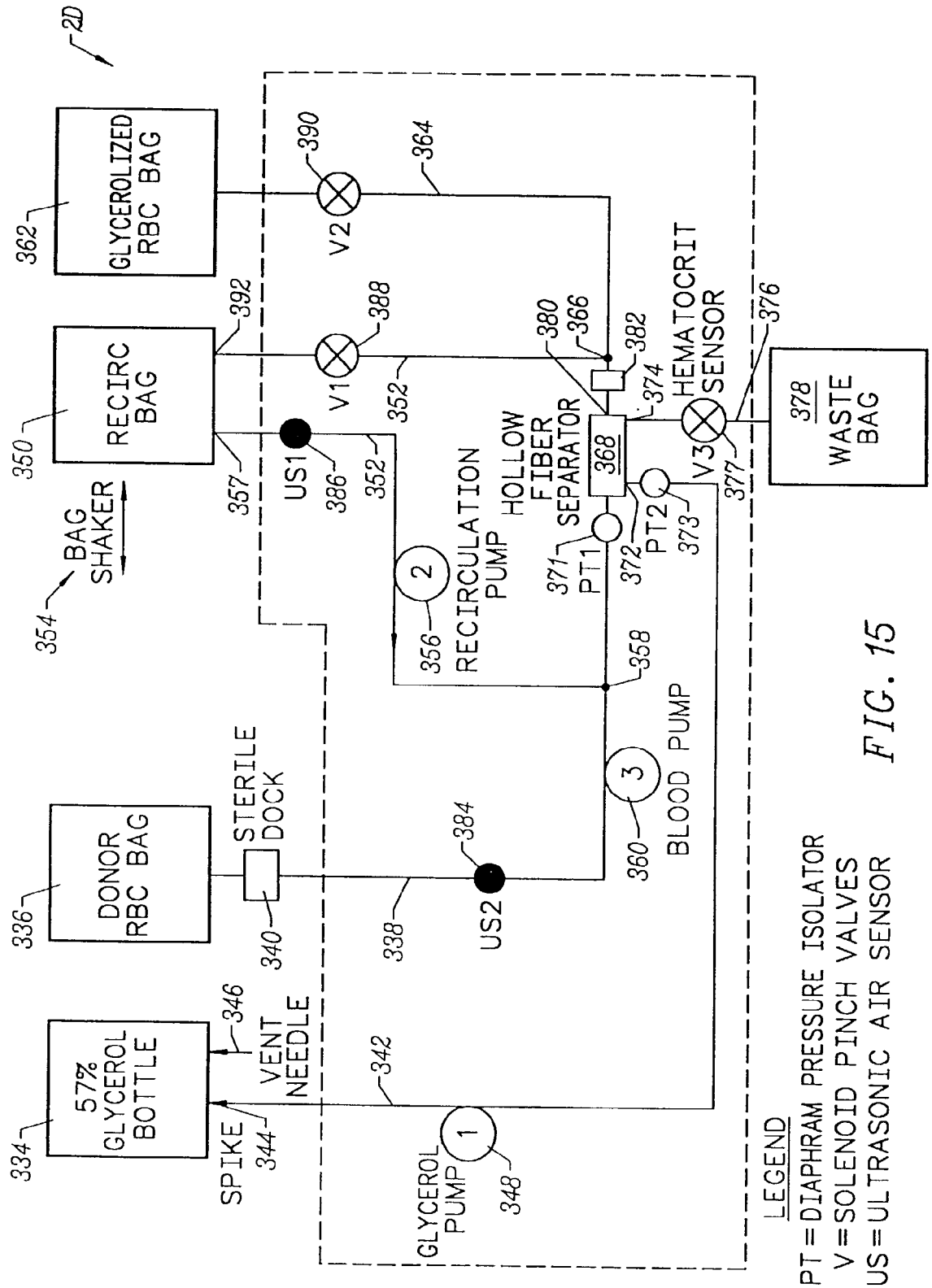
FIG. 15 illustrates a blood glycerolization processing system made according to the invention.

FIG. 15 illustrates a blood glycerolization processing system 2D in which concentrated red blood cells are stabilized by the addition of glycerol for subsequent freezing and long term storage. System 2 includes a container 334 containing, in this embodiment, a 57% glycerol solution, a red blood cell bag 336 containing concentrated red blood cells, preferably at a hematocrit of about 60 to 80%. Red blood cell bag 336 is connected to a line 338 of the cassette by a sterile dock 340 while container 334 is connected to line 342 using a conventional spike 344. Container 334 is typically not collapsible so that a conventional vent needle 346 is used to prevent a vacuum being created within container 334 as the contents are removed by glycerol pump 348 situated along line 342. A recirculation bag 350 is connected along a recirculation loop 352 of the cassette and is agitated by bag shaker 354. A recirculation pump 356 is situated along loop 352 downstream from the outlet 357 of bag 350. Loop 352 intersects with line 338 at a junction 358 positioned just downstream from a blood pump 360 along line 338. A glycerolized RBC collection bag 362, which is used to hold the glycerolized red blood cells, is connected to line 364 of the cassette, line 364 connecting to recirculation loop 352 at a junction 366. A hollow fiber separator 368 is positioned along loop 352 between junctions 358 and 366. Hollow fiber separator 368 includes a first inlet 370 downstream of junction 358 and a second inlet 372 coupled to the distal end of line 342 so that hollow fiber separator 368 is supplied both glycerol from container 334 and red blood cells from bag 336. The pressures at inlets 370, 372 are monitored by pressure isolators 371, 373. Hollow fiber separator 368 also includes a waste exit 374 connected to a waste line 376. Waste line 376 has a pinch valve 377 between exit 374 and a waste bag 378. The hematocrit of the flow exiting the main exit 380 of hollow fiber separator 368 is sensed by a hematocrit sensor 382 for control purposes. Also, ultrasonic air sensors 384, 386 are positioned along line 338 and loop 352 to sense when air is being pumped along those lines indicating that bag 336 or bag 350 is or may be empty. Solenoid pinch valve 388, 390 are used along loop 352 between entrance 392 to bag 350 and junction 366 and along line 364 between bag 362 and junction 366.

The glycerolization process of system 2D of FIG. 15 begins by pumping the blood, specifically concentrated red cells (at about a 60–80% hematocrit) which contains some plasma and possibly anticoagulant, along line 338, through first inlet 370 and through the interiors of the porous hollow fibers housed within the interior of separator 368. Simultaneously with this pumping of blood through separator 368, glycerol solution is being pumped from container 334 by pump 348 along line 342, through second inlet 372 and into that portion of the interior of separator surrounding the hollow fibers; pinch valves 377, 390 are closed and pinch valve 388 is opened when pumps 348, 360 are operating. This causes glycerol to be forced through the porous walls of the hollow fibers and into the blood flowing through the hollow fibers. In this way glycerol is quickly added to and mixed with the blood, which is important to prevent hemolysis. Separator 368 is thus initially used as a mixing device for mixing glycerol with blood. The glycerol is metered into the blood by controlling the flow rates of blood and glycerol to get a desired concentration of glycerol and red blood cells. This blood and glycerol mixture in separator 368 passes through main exit 380, along loop 352 and into recirculation bag 350.

Once all blood has been recovered from bag 336, the blood and glycerol mixture is collected in bag 350, pumps 348, 360 are stopped, pinch valve 377 is opened and recirculation pump 356 is operated to pump the blood and glycerol mixture through separator 368 while measuring the hematocrit at hematocrit sensor 382. Excess glycerol, plasma and other liquid mixed with the red cells passes from the inside to the outside of the porous walls of the hollow fibers, passes through waste exit 374, along waste line 376 and into waste bag 378. This recirculation through loop 352 continues until the desired hematocrit, sensed by sensor 382, is reached. The concentrated red cells and glycerol may be left in recirculation bag 350 or may be pumped into bag 362, whichever bag is used specifically to freeze and store the glycerolized red cells.

One of the purposes for initially adding excess amounts of glycerol is to aid removing most of the plasma and other liquid which is found in the blood in bag 336. The glycerolizing process also forces liquid out of the red cells replacing most or some of this liquid within the cells by glycerolizing liquid; this is desirable for effective frozen storage of the red cells. Removal of this liquid is also aided by adding and then removing excess glycerol.

Figure 16:
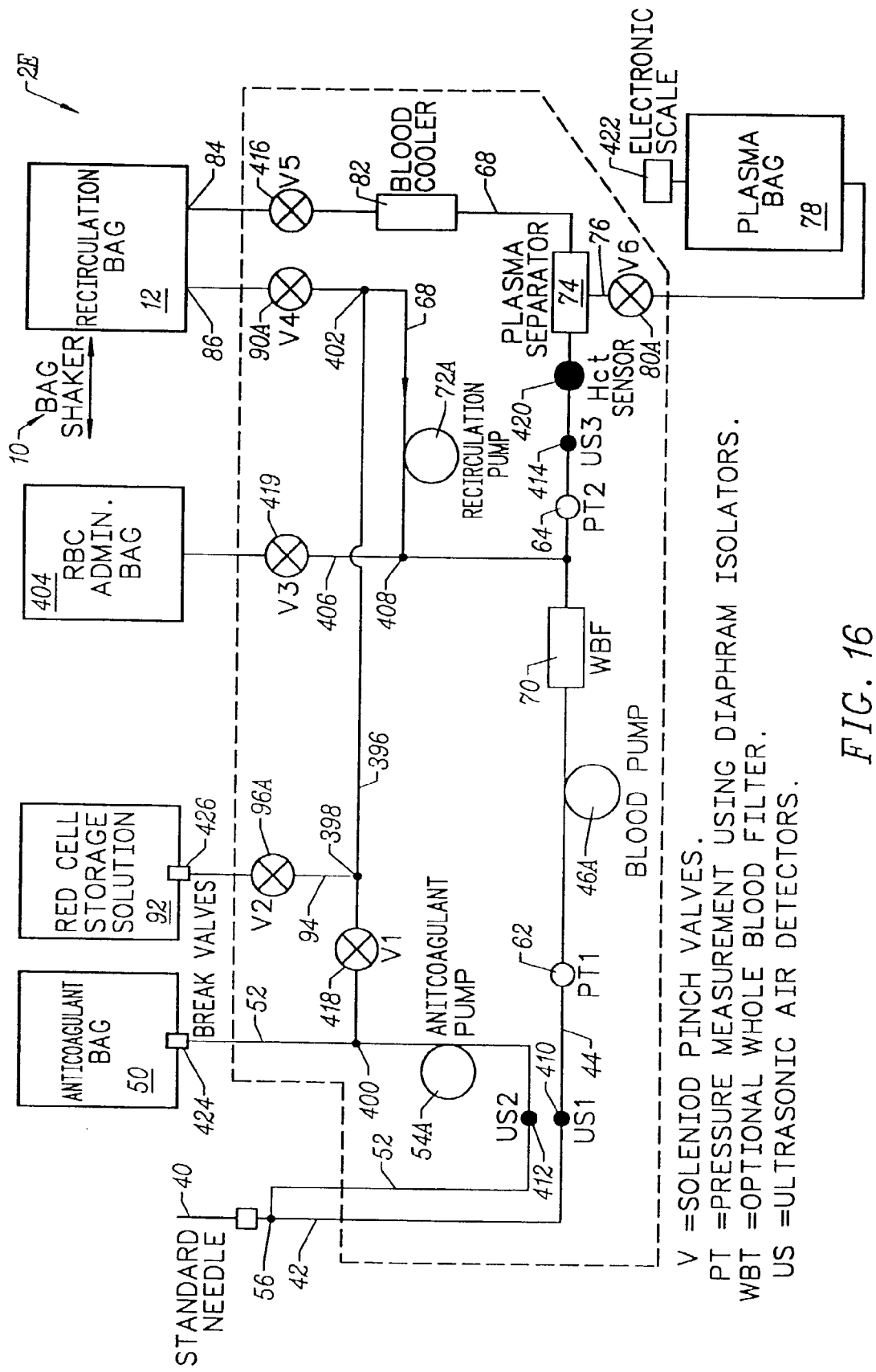
FIG. 16 illustrates an alternative embodiment of the automatic blood collection system of FIG. 2A.

FIG. 16 illustrates an alternative embodiment of the automatic whole blood collection system 2 of FIG. 2A with like elements referred to with like reference numerals. System 2E differs from system 2 in several ways. Whole blood filter 70 has been moved out of recirculation loop 68 so that it is now between junction 66 and blood pump 46A. Line 94 no longer connects to line 44 at junction 98; rather, line 94 connects to a line 396 at a junction 398. Line 396 also connects to lines 52 and 68 at junctions 400 and 402, respectively. In addition, an RBC administration bag 404 is used to receive the concentrated red cells after storage solution from bag 92 has been added by pumping the mixture out of recirculation bag 12 and into bag 404. Bag 404 is connected to a line 406 on the cassette which connects to loop 68 at a junction 408. Air in the lines is sensed by three different ultrasonic air detectors 410, 412, 414 positioned along lines 44, 52 and 68, respectively. Additional pinch valves 416, 418 and 419 are used along recirculation loop 68 and lines 396 and 406, respectively. A hematocrit sensor 420 is used along recirculation loop 68 just upstream of plasma separator 74. An electronic scale 422 is used to monitor the weight of plasma bag 78 so to provide the controller with appropriate information as to the weight of the contents of the bag. Break valves 424, 426 are used to couple bags 50 and 92 to lines 52 and 94. Bags 12, 404 and 78 are, in this embodiment, preattached to the cassette during manufacture.

The use of whole blood filter 70 is not necessary when red blood cell administration bag 404 is replaced by a separation bag that is used in an automated blood component separation system sold by Mission Medical, Inc. of Fremont, Calif. as Mission 3000 disposable set. This centrifugal automated blood component separation system will serve the function of a whole blood filter by removing leukocytes from red blood cells. An example of such a centrifuged separation bag is described in U.S. Patent Application No. 60/143,036, filed Jul. 9, 1999.

Figure 17:
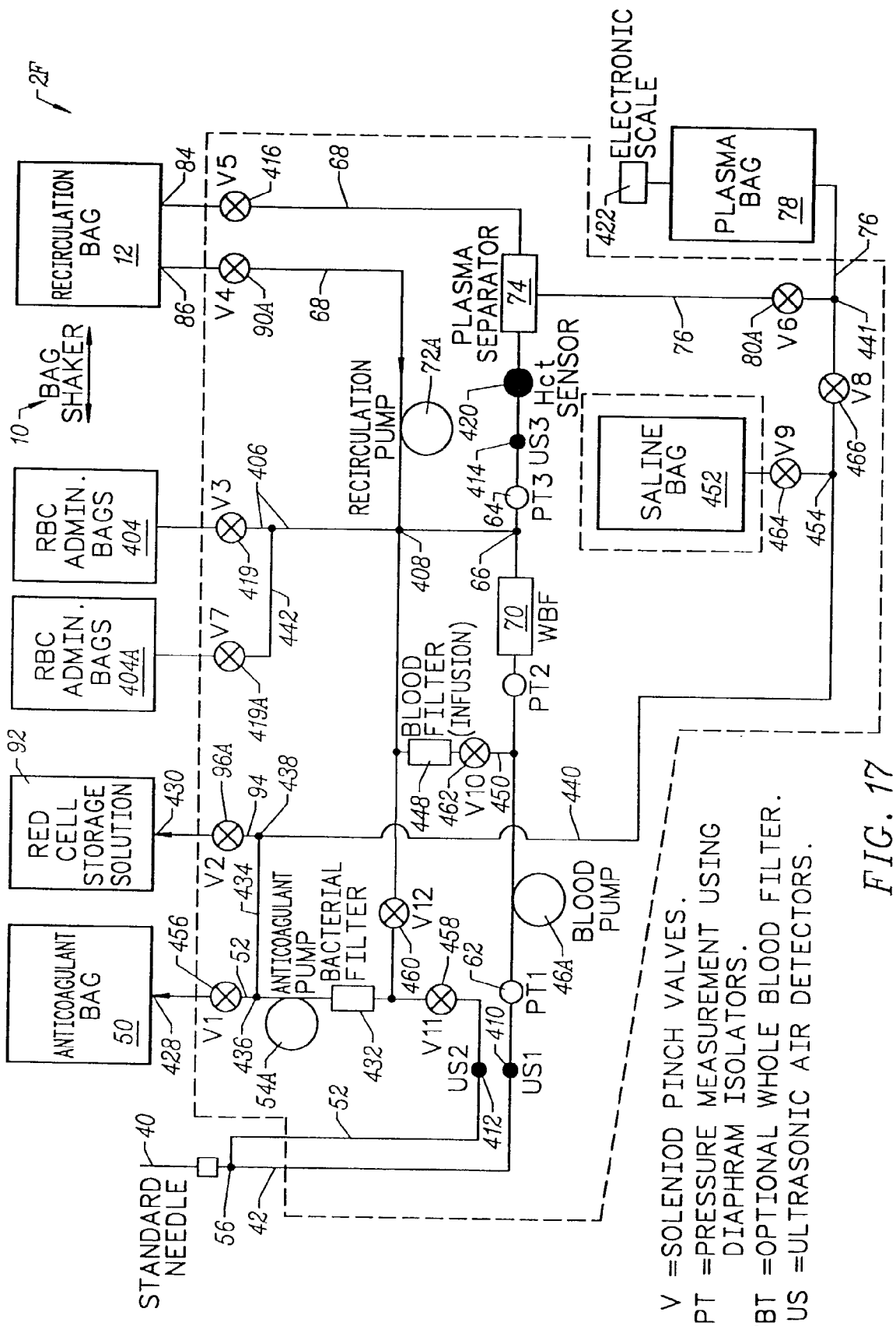
FIG. 17 illustrates an alternative embodiment of the automatic blood collection system of FIG. 16 which permits two units of blood to be collected from a single donor.

FIG. 17 illustrates an alternative embodiment of the automatic blood collection system 2E of FIG. 16 with like reference numerals referring to like elements. Bags 50 and 92 are connected to lines 52 and 92 by spikes 428, 430 rather than being preattached to the cassette. When anticoagulant bag 50 is not preattached, a bacterial filter 432 is used preferably along line 52 to prevent the introduction of bacteria into the system. A line 434 is used to couple a junction 436 along line 52 with the terminal end 438 of line 94. A line 440 couples terminal end 438 of line 94 with a junction 441 along line 76. A second RBC administration bag 404A is used and is connected to line 406 by a line 442. A line 444 couples junction 408 along recirculation loop 68 and a junction 446 along line 52. A blood filter 448 is positioned along a line 450 connecting lines 444 and 44. Blood filter 448 is used when red cells are being returned to the donor, that is during the collection of plasma as is discussed in more detail below. A saline bag 452, which as indicated in FIG. 17 is not a part of the cassette, it is coupled to line 440 via a line 454. In addition to the above described elements, six solenoid pinch valves are used with system 4F. In particular, pinch valve 456 is used between junction 436 and spike 428 along line 52, pinch valve 458 is used between junction 446 and ultrasonic air detector 412, pinch valve 460 is used along line 444, pinch valve 462 is used along line 450, pinch valve 464 is used along line 454 and pinch 466 is used along line 440 between junction 442 and line 454.

System 2F permits the collection of two units of whole blood. After the first unit of whole blood has been collected and separated, the plasma from the first unit is returned to the donor along with saline so that the donor suffers no change in total liquid volume within their circulatory system. This is repeated for the second unit of blood. System 2F is used as follows.

The collection of each unit of whole blood is done in the same fashion as described in FIGS. 2A and 16. A number of components have been added so that after one unit has been collected and separated in the recirculation bag 12, the red cells are pumped into an administration bag 404, 404A and storage solution from bag 92 is used to obtain long-term (about 35–42 days) refrigerated red cell storage. First, storage solution from bag 92 is added through the plasma separator 74 and into the recirculation bag 12 partly to purge the separator and partly simply to add the red cell storage solution to bag 12. The blood is then pumped out of the recirculation bag 12 into one of the RBC administration bags 404, 404A. It is also feasible to use the anticoagulant from bag 50 instead of the red cell storage solution from bag 92. Either the red cell storage solution or the anticoagulant are pumped by the anticoagulant pump 54A through the bacterial filter 432, through valve 460, through plasma separator 74 and then into the recirculation bag 12. Either one of the anticoagulant or the storage solution can perform the purging function so the red cell storage solution may be used only when long-term storage is desired.

The next step is to pump the plasma out of the plasma bag 78 back into the donor. To do that anticoagulant pump 54A is used with valve 466 open and valves 80A and 464 closed. Plasma is pumped out of the plasma bag 78, through the bacterial filter 432, through open valve 458 and back into the donor through needle 40. In this case the blood pump 46A is off and acts as a valve so that the flow goes into the donor and not back into the system. Ultrasonic sensor 412 is used to detect when the plasma bag 78 is empty, which is when air bubbles arrive in sensor 412, so flow is terminated when blood plasma bag 78 is empty. Then valve 466 closes, valve 464 opens, and saline is pumped through the same route, that is the anticoagulant pump 54A through the bacterial filter 432 and through open valve 458 back to the donor until the plasma plus the saline returned to the donor add up to the amount of whole blood removed from the donor.

In the event plasma is to be retained and not given back to the donor, it may be necessary to give red cells back to the donor. That can be accomplished by pumping blood out of the recirculation bag 12 or a red cell administration bag 404, 404A using either the recirculation pump 72A and the blood pump 46A pumping through the blood infusion filter 448 and open valve 462 back to the donor through needle 40. If the blood has been put into one of the RBC administration bags 404, 404A, then it is pumped through the blood filter 70 and open valve 462 by the blood pump 46A. Blood infusion filter 448 is only used when pumping red cells back into the donor. Filter 448 is a particulate filter with a pore size of 20–80 microns intended to remove particulates from red cells that are given back to the donor.

Figure 18:
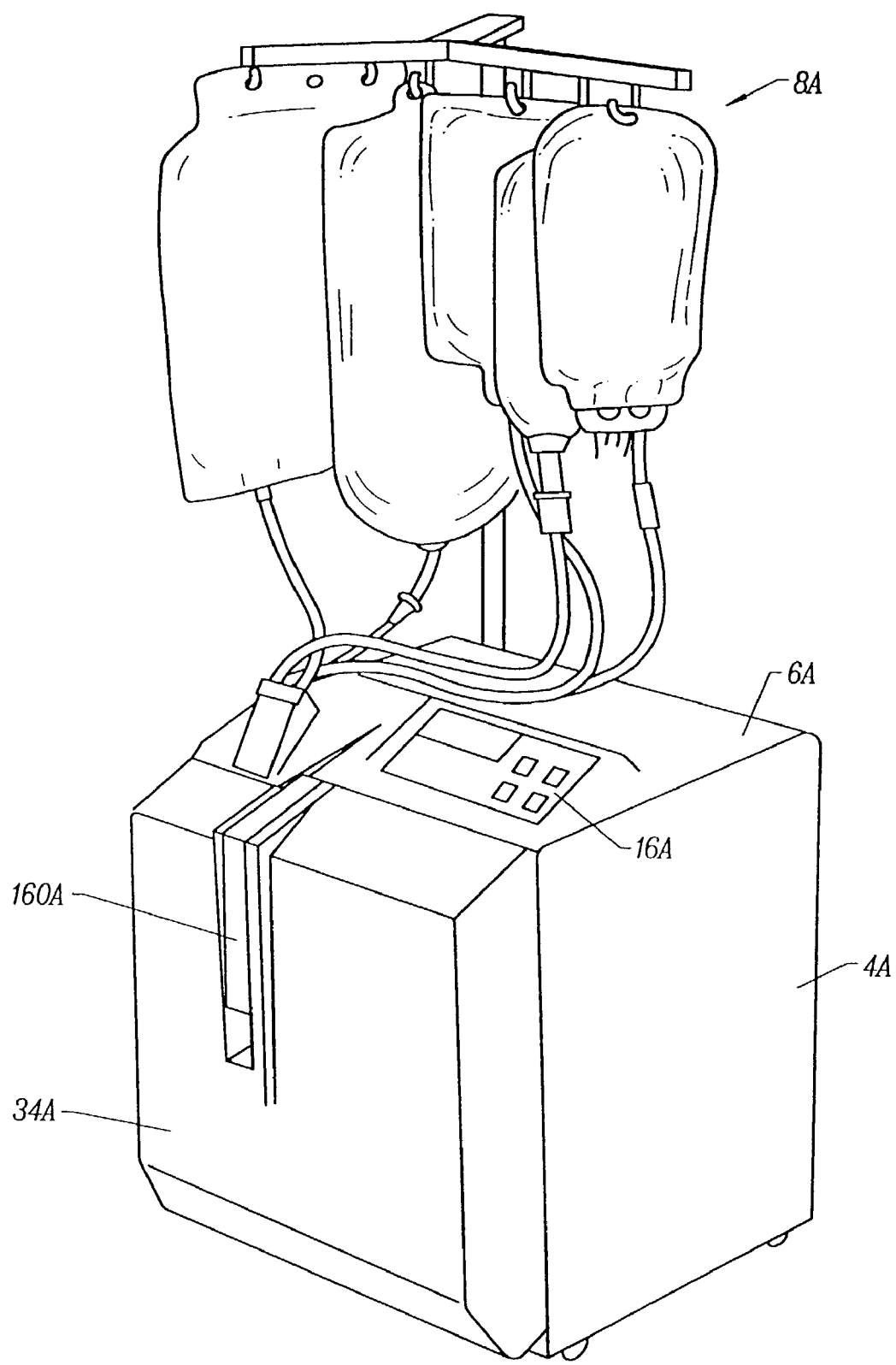
FIG. 18 is an overall view of an alternative embodiment of the system of FIG. 1.
Figure 19:
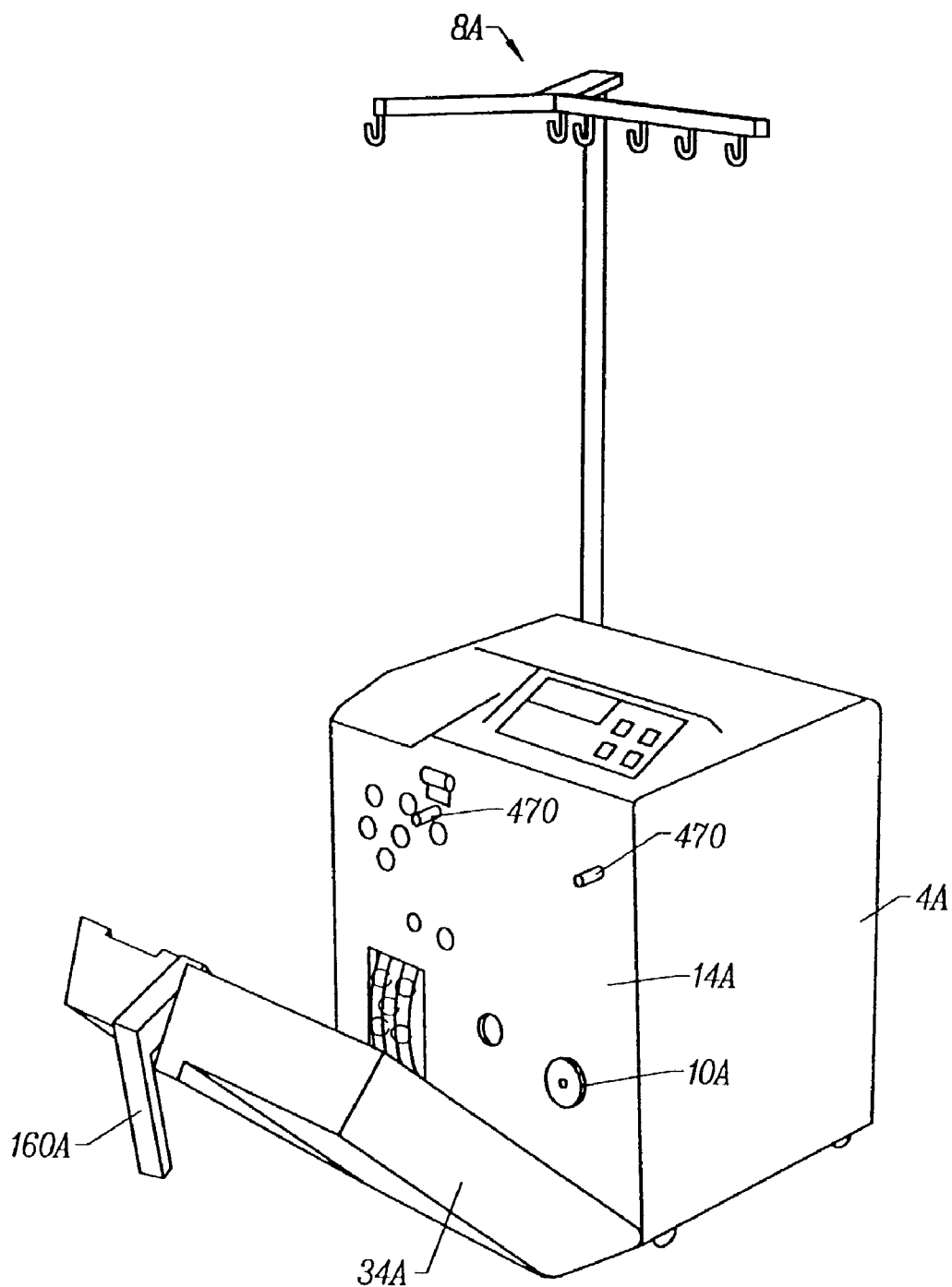
FIG. 19 is a view of the system of FIG. 18 with the front door open, the cassette removed from between the front door and the front panel and the various bags coupled to the cassette removed from the bag hanger.
Figure 20:
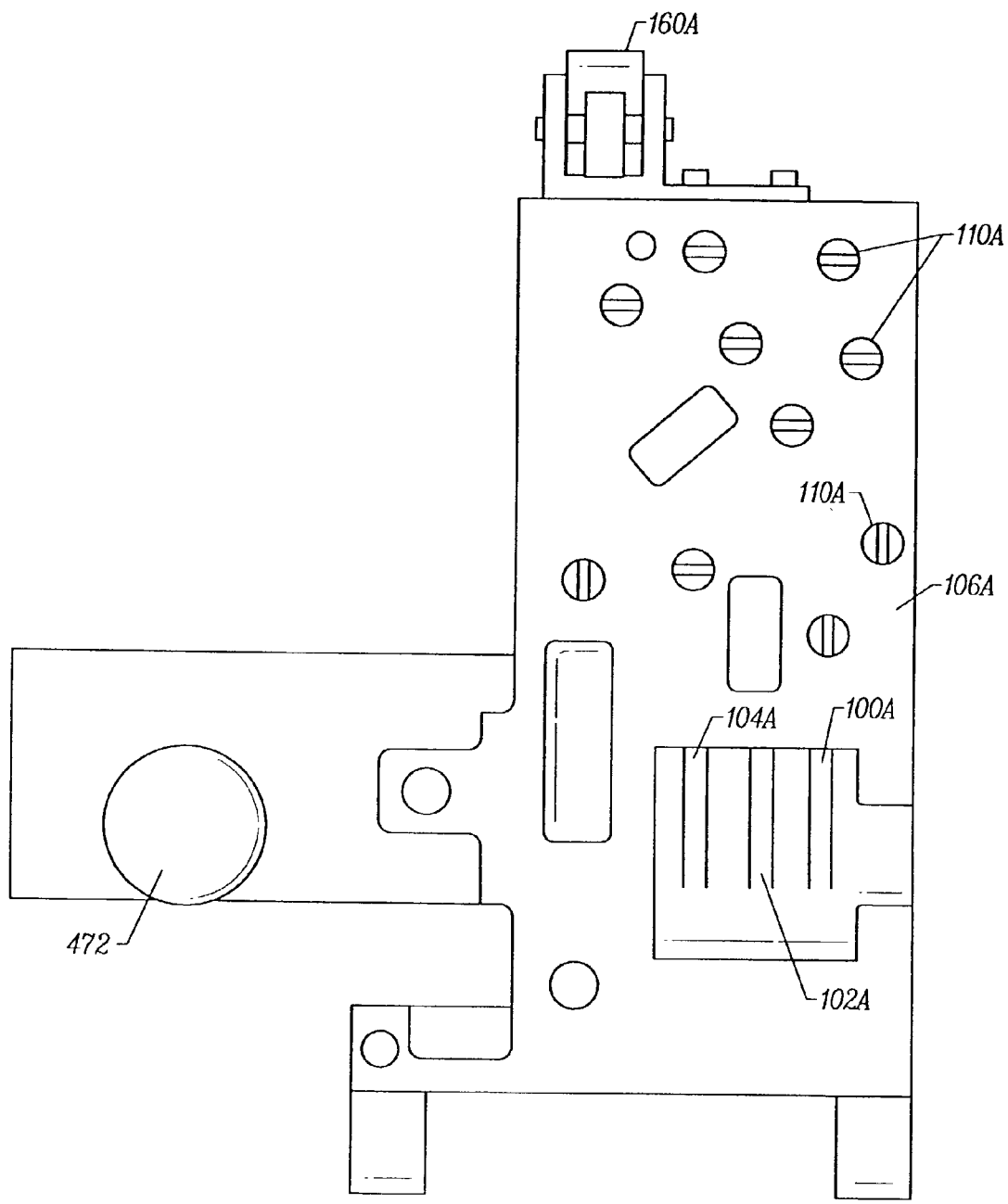
FIG. 20 is a view of a portion of the front door of FIG. 19 similar to the view of FIG. 4 illustrating a bag shaker support surface positioned opposite a reciprocating bag shaker shown in FIG. 19.

FIGS. 18–20 illustrate an automated blood system 2G made according to the invention. Note the system 2G can be used for any of the above-discussed blood processing methods through the appropriate choice of programs and the use of the appropriate cassette and bags. System 2G will be discussed very briefly pointing out certain similarities and differences with system 2 as shown in FIG. 1 with like reference numerals referring to like elements. Housing 4A includes a user control panel 16A mounted to a sloped portion of the top 6A of the housing as opposed to its front panel 14A as in the FIG. 1 embodiment. Door 34A covers the entire front panel 14A when in the closed position of FIG. 18 and is maintained in the closed position by being latched with handle 160A. FIG. 19 illustrates system 2G but with the cassette, bags and associated tubing removed for clarity of illustration. Instead of being slideably mounted to a cassette 24 as shown in FIG. 2, the cassette is hung against front panel 14A by a pair of outwardly extending pins 470. Also, instead of using a bag manipulator 10 above housing 4 as in FIG. 1, the contents of recirculation bag 12, also called storage bag 12, are agitated by the movement of a bag shaker 10A extending from front panel 14A with bag 12 being captured between bag shaker 10A and a bag shaker support surface 472, shown in FIG. 20.

As used herein, blood typically includes whole blood, concentrated red blood cells, glycerolized blood and other blood products including a substantial portion of red blood cells.

Modification and variation can be made to the described embodiments without departing from the subject of the invention as defined by the following claims. For example, the door or the cassette assembly, or both, could be designed to be completely removable from the housing rather than being pivotally mounted to the housing. The roller tracks or the pinch surfaces, or both, could be formed as a part of the cassette assembly instead of the door. Ultrasonic, as well as other remote-sensing flow detectors, may be used to detect fluid flows along the various pathways. In the autotransfusion system 2A of FIG. 12, the hematocrit can be measured using a hematocrit sensor just downstream of blood pump 174 instead of the use of laminar flow tube 176, together with pressure access ports 178, 180.

Any and all patents, applications and printed publications referred to above are incorporated by reference.

What is claimed is:

1. A blood washing system comprising:
an endless recirculation loop, fluidly coupled to an inlet for a source of blood;
a blood separator, having an entrance port, an exit port and a removed fraction port, defining a portion of the recirculation loop between the entrance and exit ports;
a pump situated along the recirculation loop operable to pump blood from and through the recirculation loop;

the blood separator configured to separate blood entering the entrance port into a retained fraction, which passes through the exit port, and a removed fraction, which passes through the removed fraction port, at least a portion of the retained fraction passing through the blood separator at least a second time;

a replacement fluid source fluidly coupled to the recirculation loop, whereby the replacement fluid source is configured to replace at least a part of the removed fraction; and control means programmed to control the addition of replacement fluid so as to regulate hematocrit of the fluid in the recirculation loop, wherein the hematocrit is determined by measuring resistance to flow within the blood separator.

2. The system according to claim 1 wherein the control means acts to maintain said hematocrit within a desired range.

3. The system according to claim 1 wherein the removed fraction comprises at least one of plasma, free plasma hemoglobin, leukocytes, and viral inactivation compounds.

4. The system according to claim 1 wherein the retained fraction comprises red blood cells.

5. The system according to claim 1 wherein the retained fraction comprises plasma.

6. The system according to claim 1 wherein the replacement fluid is saline.

7. The system according to claim 1 wherein the replacement fluid includes glucose.

8. The system according to claim 1 wherein the pump stops when the amount of blood taken from the source has reached a predetermined amount and then the blood separator stops when the hematocrit has reached a predetermined hematocrit.

9. The system according to claim 1 wherein the source of blood is a chosen one of a donor vein, a patient's surgery site, a container of concentrated red blood cells and a container of thawed blood.

10. A method for washing blood comprising:
accessing a source of blood;
pumping blood from the source of blood through a recirculation loop, the recirculation loop comprising a blood separator;
separating the blood passing through the blood separator into a removed fraction and a retained fraction;
removing the removed fraction from the recirculation loop;
said pumping step being carried out so that at least a portion of the retained fraction passes through the blood separator at least a second time;
adding a replacement fluid to the recirculation loop;
determining a desired hematocrit of the blood in the recirculation loop by measuring resistance to flow within the blood separator; and
the adding step comprising controlling the amount of the replacement fluid added according to the desired hematocrit of the blood in the recirculation loop.

11. The method according to claim 10 wherein the removed fraction comprises at least one of plasma, free plasma hemoglobin, leukocytes, and viral inactivation compounds.

12. The method according to claim 10 wherein the retained fraction comprises red blood cells.

13. The system according to claim 10 wherein the retained fraction comprises plasma.

14. The method according to claim 10 wherein the replacement fluid is saline.

15. The method according to claim 10 wherein the replacement fluid includes glucose.

16. The method according to claim 10 wherein the blood pumping step is stopped when the amount of blood taken from the source has reached a predetermined amount and then the blood separating step is stopped when the desired hematocrit has reached a predetermined hematocrit.

17. The method according to claim 10 wherein the accessing step is carried out by fluidly coupling the recirculation loop with an inlet for a source of blood, the source of blood being a chosen one of a donor vein, a patient's surgery site, a container of concentrated red blood cells and a container of thawed blood.

18. The system according to claim 10 wherein the desired hematocrit is at least about 45%.

19. The system according to claim 10 where in the desired hematocrit is about 60–80%.

* * * * *